(12) United States Patent  (10) Patent No.: US 8,016,817 B2
Santini, Jr. et al.  (45) Date of Patent: Sep. 13, 2011

(54) DEVICE FOR CONTROLLING EXPOSURE OF RESERVOIR CONTENTS TO SURROUNDINGS

(75) Inventors: John T. Santini, Jr., North Chelmsford, MA (US); Michael J. Cima, Winchester, MA (US); Scott A. Uhland, Medford, MA (US)

(73) Assignee: MicroCHIPS, Inc., Waltham, MA (US)

( * ) Notice: Subject to any disclaimer, the term of this patent is extended or adjusted under 35 U.S.C. 154(b) by 127 days.

(21) Appl. No.: 12/348,609

(22) Filed: Jan. 5, 2009

(65) Prior Publication Data

US 2009/0112188 A1   Apr. 30, 2009

Related U.S. Application Data

(63) Continuation of application No. 10/747,900, filed on Dec. 29, 2003, now Pat. No. 7,473,248, which is a continuation of application No. 10/341,305, filed on Jan. 13, 2003, now Pat. No. 6,669,683, which is a continuation of application No. 09/638,109, filed on Aug. 11, 2000, now Pat. No. 6,527,762.

(60) Provisional application No. 60/149,493, filed on Aug. 18, 1999.

(51) Int. Cl.
*A61K 9/22* (2006.01)
(52) U.S. Cl. .................................. 604/890.1
(58) Field of Classification Search ............... 604/890.1, 604/113, 114, 891.1, 892.1, 19; 216/2, 39, 216/56
See application file for complete search history.

(56) References Cited

U.S. PATENT DOCUMENTS

| | | | |
|---|---|---|---|
| 5,167,625 A | 12/1992 | Jacobsen et al. | |
| 5,196,002 A | 3/1993 | Hanover et al. | |
| 5,200,051 A | 4/1993 | Cozzette et al. | |
| 5,252,294 A | 10/1993 | Kroy et al. | |
| 5,366,454 A | 11/1994 | Currie et al. | |
| 5,368,704 A | 11/1994 | Madou et al. | |
| 5,443,508 A | 8/1995 | Giampapa | |
| 5,490,962 A | 2/1996 | Cima et al. | |
| 5,797,898 A | 8/1998 | Santini, Jr. et al. | |
| 6,114,658 A | 9/2000 | Roth et al. | |
| 6,123,861 A | 9/2000 | Santini, Jr. et al. | |
| 6,178,349 B1 | 1/2001 | Kieval | |
| 6,247,485 B1 | 6/2001 | Rossi et al. | |
| 6,349,232 B1 | 2/2002 | Gordon | |
| 6,491,666 B1 | 12/2002 | Santini, Jr. et al. | |
| 6,527,762 B1 * | 3/2003 | Santini et al. ............. | 604/890.1 |
| 6,537,256 B2 | 3/2003 | Santini, Jr. et al. | |
| 6,551,838 B2 | 4/2003 | Santini, Jr. et al. | |
| 6,571,125 B2 | 5/2003 | Thompson | |

(Continued)

FOREIGN PATENT DOCUMENTS

DE   19716683   6/1998

(Continued)

*Primary Examiner* — Manuel A Mendez
(74) *Attorney, Agent, or Firm* — Sutherland Asbill & Brennan LLP

(57) ABSTRACT

Microchip devices are provided that include a substrate; a plurality of reservoirs in the substrate, each reservoir defining an internal volume; and a reservoir cap positioned on or in each of the reservoirs bounding the internal volume from an external environment, the reservoir cap being formed of a material that undergoes a phase change upon heating, wherein the internal volume can communicate with the external environment upon heating said reservoir cap to cause said reservoir cap to undergo a phase change and rupture.

5 Claims, 16 Drawing Sheets

U.S. PATENT DOCUMENTS

| | | |
|---|---|---|
| 6,656,162 B2 | 12/2003 | Santini, Jr. et al. |
| 6,663,615 B1 | 12/2003 | Madou et al. |
| 6,669,683 B2 | 12/2003 | Santini, Jr. et al. |
| 6,730,072 B2 | 5/2004 | Shawgo et al. |
| 2002/0022826 A1 | 2/2002 | Reynolds et al. |
| 2002/0072734 A1 | 6/2002 | Liedtke |
| 2002/0072784 A1 | 6/2002 | Sheppard, Jr. et al. |
| 2002/0099359 A1 | 7/2002 | Santini, Jr. et al. |
| 2002/0107470 A1 | 8/2002 | Richards et al. |
| 2002/0111658 A1 | 8/2002 | Greenberg et al. |
| 2002/0138067 A1 | 9/2002 | Sheppard, Jr. et al. |
| 2002/0183721 A1 | 12/2002 | Santini, Jr. et al. |
| 2002/0187260 A1 | 12/2002 | Sheppard, Jr. et al. |
| 2003/0010808 A1 | 1/2003 | Uhland et al. |
| 2003/0036794 A1 | 2/2003 | Ragheb et al. |
| 2003/0069560 A1 | 4/2003 | Adamis et al. |
| 2003/0104590 A1 | 6/2003 | Santini, Jr. et al. |
| 2004/0043042 A1 | 3/2004 | Johnson et al. |
| 2004/0082937 A1 | 4/2004 | Ausiello et al. |

FOREIGN PATENT DOCUMENTS

| | | |
|---|---|---|
| JP | 1285274 | 11/1998 |
| WO | 02056862 | 7/2002 |

* cited by examiner

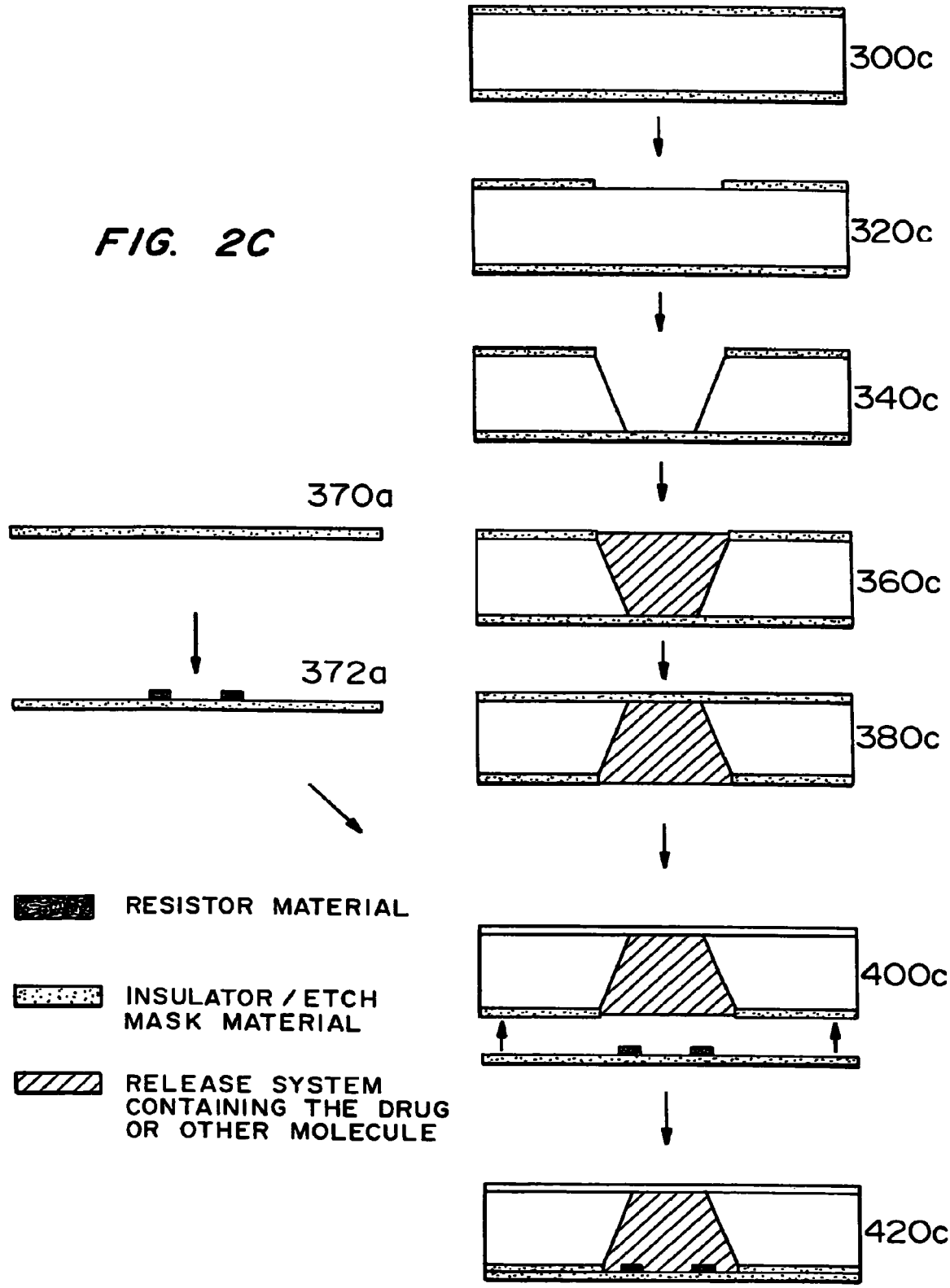

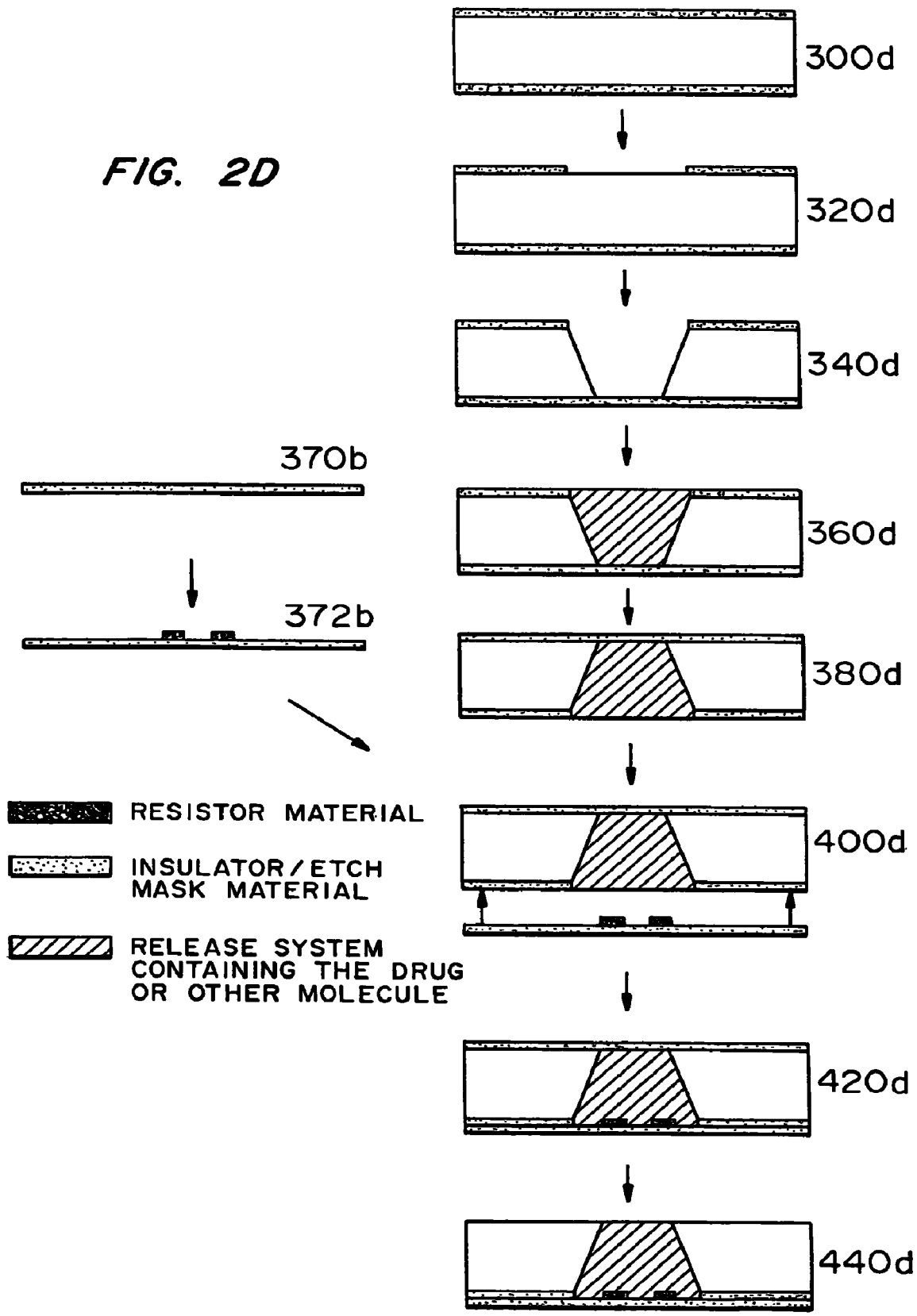

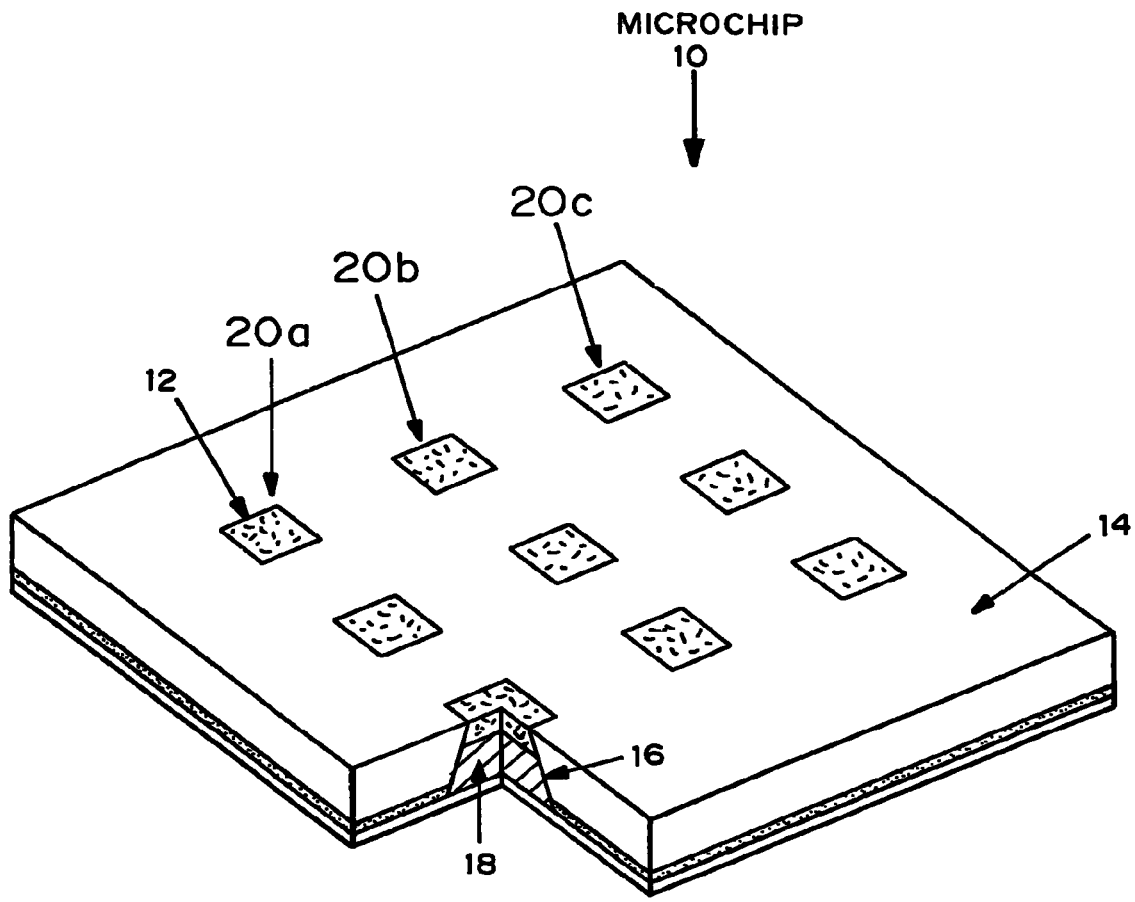
|  | RELEASE SYSTEM CONTAINING THE DRUG OR OTHER MOLECULE |
| 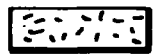 | RESERVOIR CAP MATERIAL |
|  | INSULATOR/ETCH MASK MATERIAL |
FIG. 4

FIG. 5
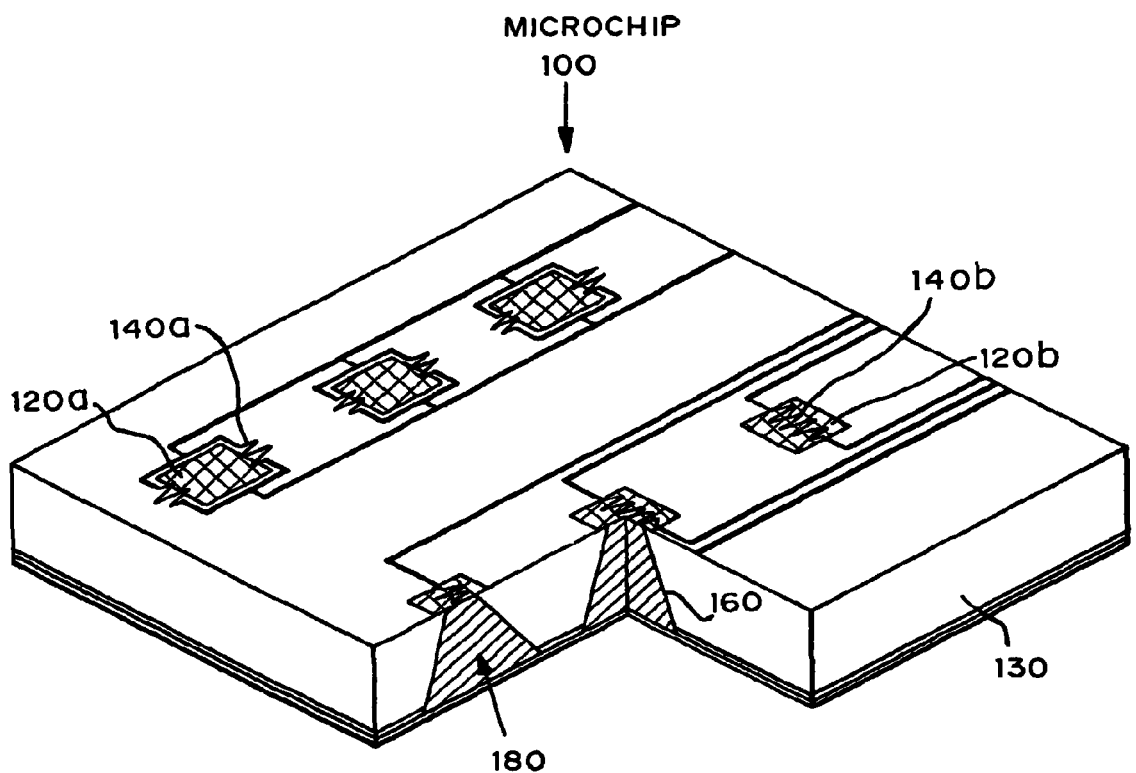
 RESISTOR MATERIAL
 CAP MATERIAL
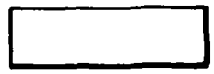 INSULATOR / ETCH MASK MATERIAL
 RELEASE SYSTEM CONTAINING THE DRUG OR OTHER MOLECULE

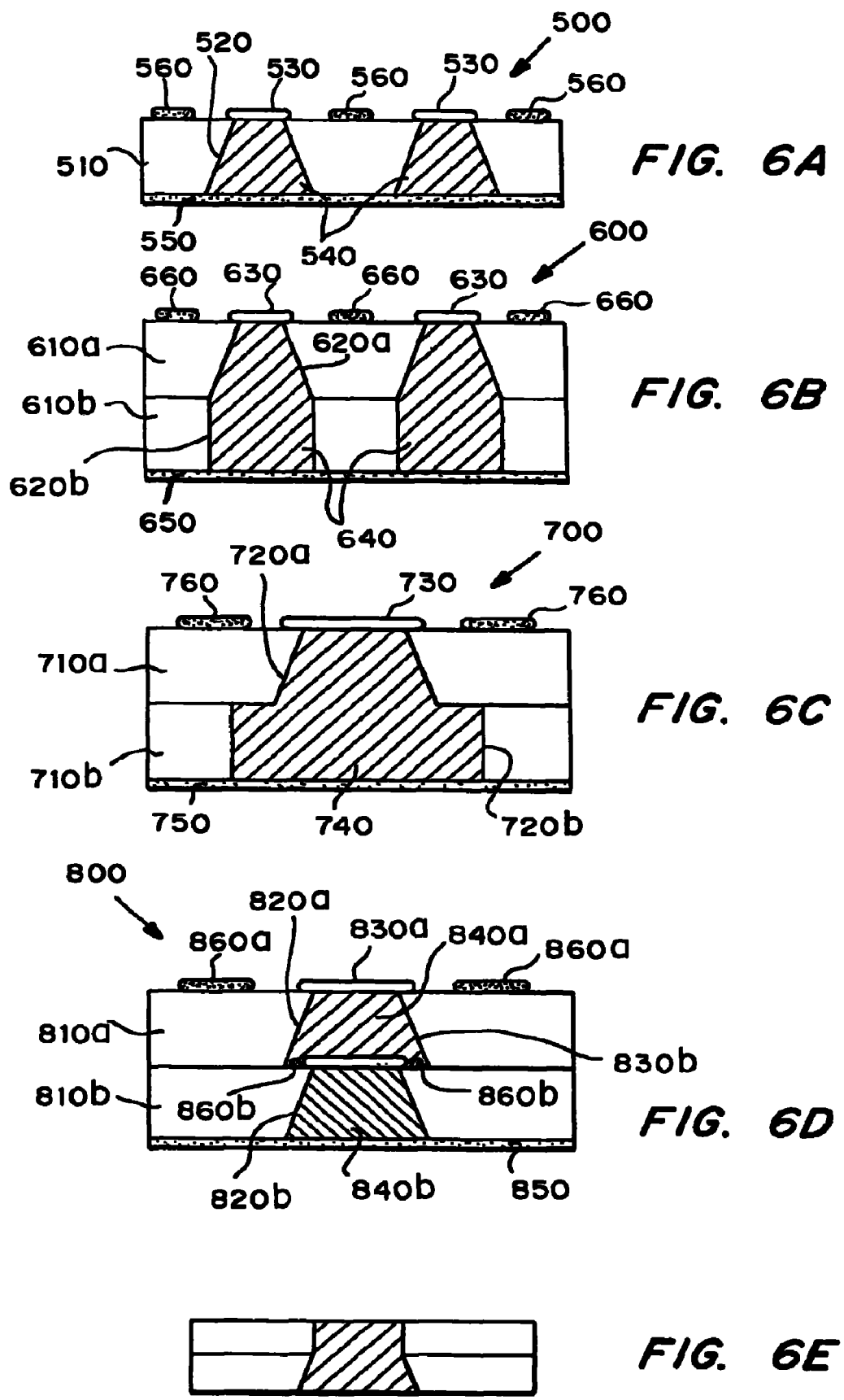

FIG. 7A
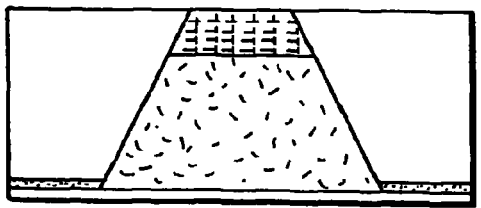
FIG. 7B
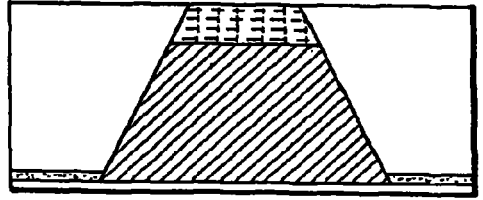
FIG. 7C
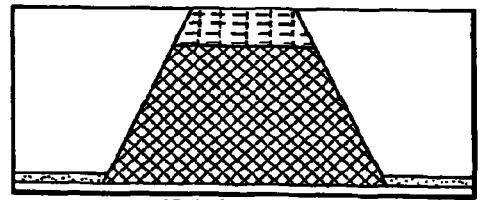
FIG. 7D
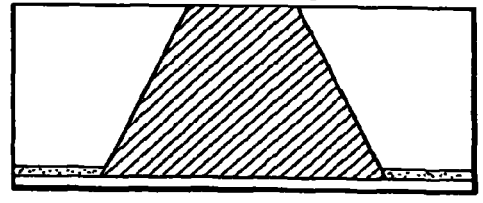
FIG. 7E
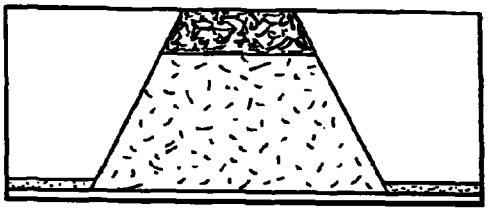
FIG. 7F
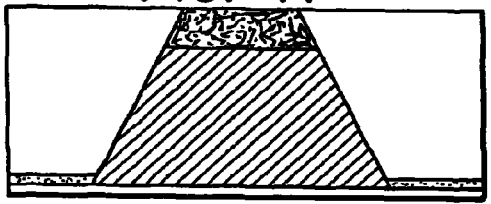
FIG. 7G
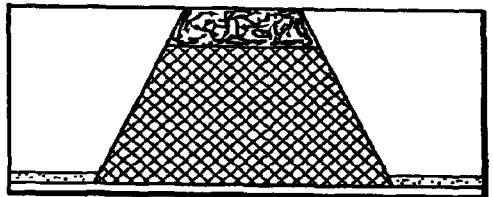
FIG. 7H
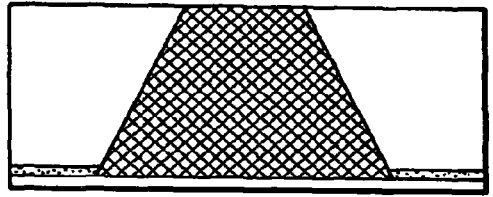
FIG. 7I
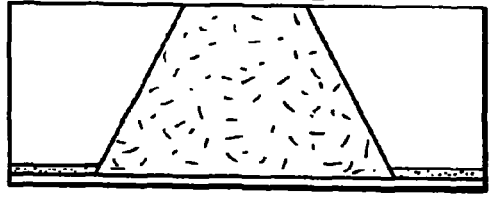
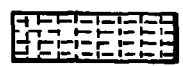 DEGRADABLE RESERVOIR CAP MATERIAL
 NON-DEGRADABLE RESERVOIR-CAP MATERIAL
 DEGRADABLE RELEASE SYSTEM
 NON-DEGRADABLE RELEASE SYSTEM
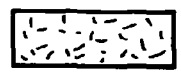 PURE DRUG OR OTHER MOLECULE (SOLID, LIQUID, OR GEL FORM)
 INSULATOR/ETCH MASK MATERIAL

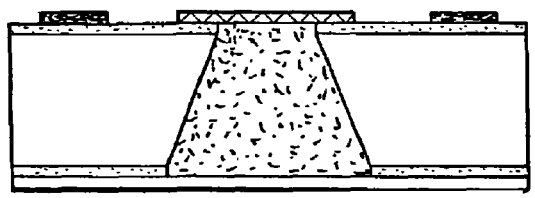
FIG. 8A
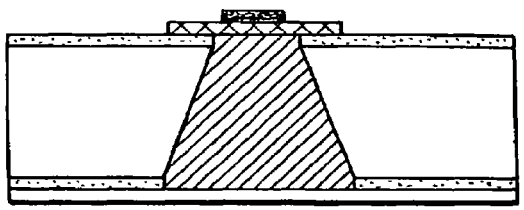
FIG. 8B
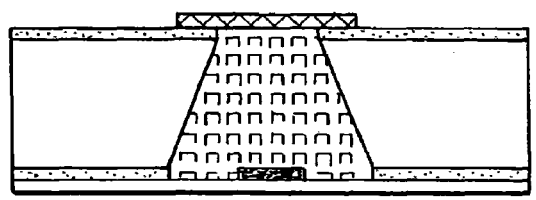
FIG. 8C
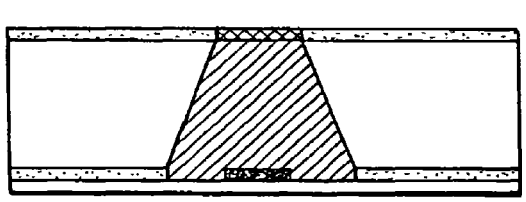
FIG. 8D
 RESISTOR
 CAP MATERIAL
 INSULATOR / ETCH MASK MATERIAL
 DEGRADABLE RELEASE SYSTEM
 NON-DEGRADABLE RELEASE SYSTEM
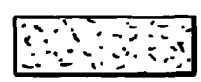 PURE DRUG OR OTHER MOLECULE (SOLID, LIQUID OR GEL FORM)

T1 < T2 < T3

- INSULATOR / ETCH MASK MATERIAL
- CAP MATERIAL
- RESISTOR
- RELEASE SYSTEM $T1 < T2 < T3$
$P1 < P2 < P3$

- INSULATOR/ETCH MASK MATERIAL
- CAP MATERIAL
- RESISTOR
- RELEASE SYSTEM

T1 < T2 < T3

DIRECTION OF FORCES ON CAP

- INSULATOR/ETCH MASK MATERIAL
- CAP MATERIAL
- RESISTOR
- RELEASE SYSTEM $T1 < TMELT < T2$

| | |
|---|---|
| ▨ | INSULATOR/ETCH MASK MATERIAL |
| ▩ | CAP MATERIAL |
| ■ | RESISTOR |
| ▧ | RELEASE SYSTEM |
| ▦ | MOLTEN CAP |

DEVICE FOR CONTROLLING EXPOSURE OF RESERVOIR CONTENTS TO SURROUNDINGS

CROSS-REFERENCE TO RELATED APPLICATIONS

This is a continuation of U.S. application Ser. No. 10/747,900, filed Dec. 29, 2003, now U.S. Pat. No. 7,473,248, which is a continuation of U.S. application Ser. No. 10/341,305, filed Jan. 13, 2003, now U.S. Pat. No. 6,669,683, which is a continuation of U.S. application Ser. No. 09/638,109, filed Aug. 11, 2000, now U.S. Pat. No. 6,527,762. Application Ser. No. 09/638,109 claims benefit of U.S. Provisional Application No. 60/149,493, filed Aug. 18, 1999. All of these applications are incorporated herein by reference in their entirety.

BACKGROUND OF THE INVENTION

This invention relates to miniaturized devices for delivery of chemical molecules, and more particularly to controlled time and rate release multi-welled delivery devices.

Drug delivery is an important aspect of medical treatment. The efficacy of many drugs is directly related to the way in which they are administered. Some therapies require that the drug be repeatedly administered to the patient over a long period of time. This makes the selection of a proper drug delivery method problematic. Patients often forget, are unwilling, or are unable to take their medication. Drug delivery also becomes problematic when the drugs are too potent for systemic delivery. Therefore, attempts have been made to design and fabricate a delivery device, which is capable of the controlled, pulsatile, or continuous release of a wide variety of molecules including, but not limited to, drugs and other therapeutics.

U.S. Pat. No. 5,797,898 to Santini Jr., et al. discloses microchip delivery devices which have a plurality, typically hundreds to thousands, of tiny reservoirs in which each reservoir has a reservoir cap positioned on the reservoir over the molecules, so that the molecules, e.g., drugs, are released from the device by diffusion through or upon disintegration of the reservoir caps. The reservoirs may have caps made of a material that degrades at a known rate or that has a known permeability (passive release), or the caps may include a conductive material capable of dissolving or becoming permeable upon application of an electrical potential (active release). It would be useful, however, to utilize other methods for triggering release, particularly when the presence of an electrolyte is not convenient or possible. It also would be advantageous to provide active release without the limitation that the cap material includes a conductive material capable of disintegrating or becoming permeable upon application of an electrical potential.

It would be desirable to provide a multi-welled delivery device for drugs and other molecules that does not require the presence of an electrolyte.

It would be desirable to provide a multi-welled delivery device for active release of drugs and other molecules that does not require a conductive reservoir cap or direct application of an electrical potential.

SUMMARY OF THE INVENTION

Microchip delivery devices are provided that control both the rate and time of release of molecules, wherein the device includes a substrate, at least one reservoir in the substrate containing the molecules (i.e., a release system), and a reservoir cap positioned on the reservoir over the molecules, wherein the molecules are released from the reservoir upon heating or cooling the device or a portion thereof sufficient to rupture the reservoir cap. In a preferred embodiment, the device includes a resistor integrated into the reservoir or mounted near or on the reservoir cap, which upon application of an electric current through the resistor, causes at least one of the contents of the reservoir to thermally expand, vaporize, phase change, or undergo a thermally driven reaction, such that the reservoir cap ruptures due to mechanical stress. Alternatively, the thermal trigger can be a temperature change to the entire device (e.g., without application of resistive heating) due for example to the placement onto or into the body, or otherwise caused by a significant change in the temperature of the environment in which the device is placed. In another embodiment, the device includes reservoir caps that rupture due to expansion, contraction, or phase change of the cap material in response to a temperature change. In yet another embodiment, the device includes reservoir caps or release systems that become more permeable to the molecules in response to a temperature change.

The reservoir cap preferably is a thin film of a material having a yield or tensile strength beyond which the material fails by fracture or some other form of mechanical failure. Alternatively, the reservoir cap could be made of material that loses structural integrity when it undergoes a phase change in response to a change in temperature. Examples of such materials include metals, glasses, ceramics, and polymers, such as semicrystalline polyesters.

The devices can be designed to provide release in either a continuous or pulsatile manner. The microchips provide control over the rate the molecules are released as well as the time at which release begins. In one embodiment, the thermal trigger for a reservoir can be controlled by a preprogrammed microprocessor, remote control, or by a signal from a biosensor.

The reservoirs can contain multiple drugs or other molecules in variable dosages. Each of the reservoirs of a single microchip can contain different molecules and/or different amounts and concentrations, which can be released independently. Examples of molecules to be delivered include drugs, fragrances, dyes or coloring agents, sweeteners, diagnostic reagents, and compounds used in tissue culture, such as cellular growth factors.

BRIEF DESCRIPTION OF THE DRAWINGS

FIGS. 2a-d depicts, in cross-sectional views, various fabrication schemes for active delivery devices.

FIG. 4 shows, in a perspective and partial cross-sectional view, one embodiment of a passive delivery device.

FIG. 5 shows, in a perspective and partial cross-sectional view, one embodiment of an active delivery device.

FIGS. 6a-e are cross-sectional schematic views of various embodiments of devices having substrates formed from two fabricated substrate portions which have been joined together.

FIGS. 7a-i are cross-sectional schematic views of several configurations of passive delivery devices.

FIGS. 8a-d are cross-sectional schematic views of several configurations of active delivery devices.

DETAILED DESCRIPTION OF THE INVENTION

Figure 1:
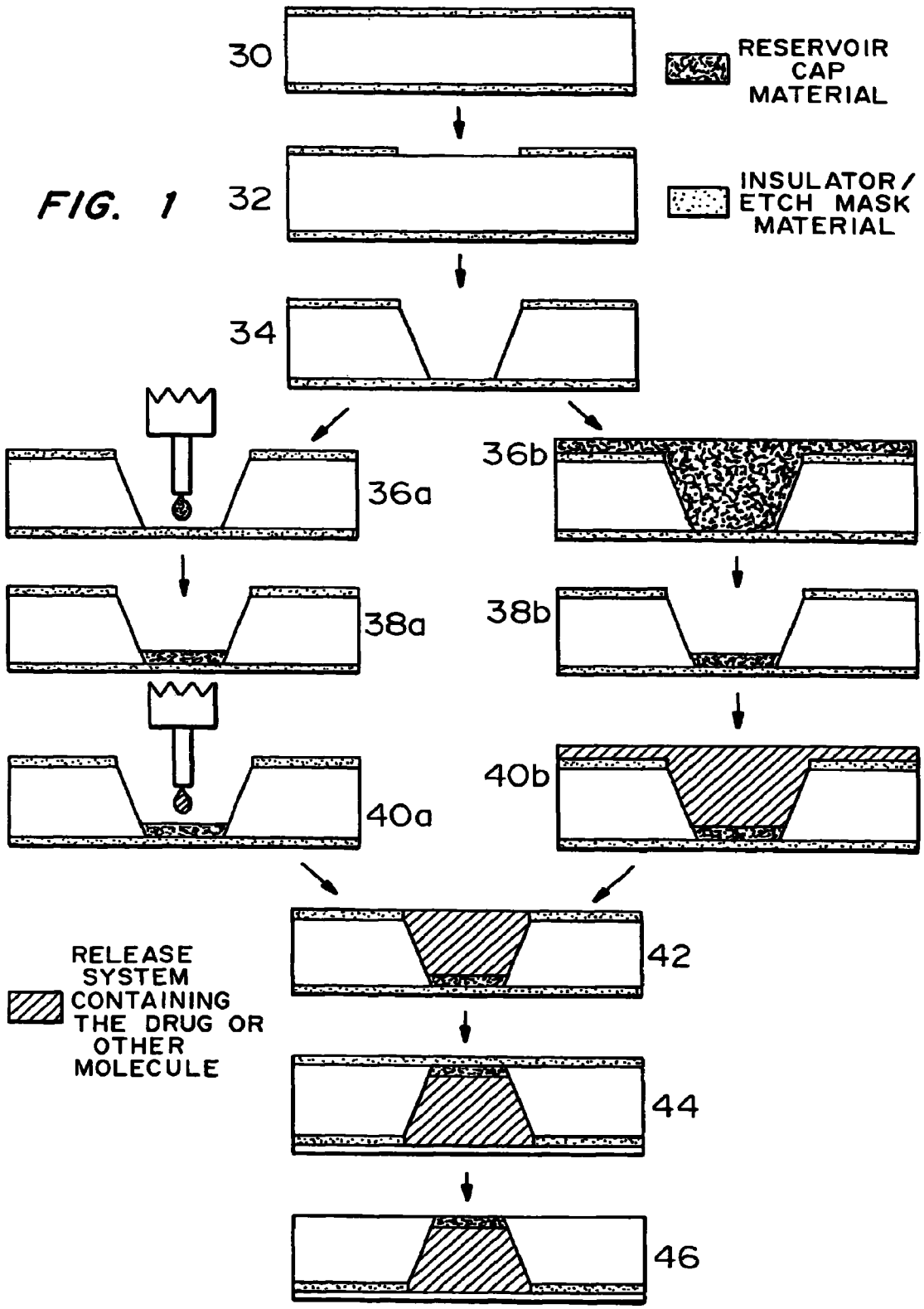
FIG. 1 depicts, in a cross-sectional view, a typical fabrication scheme for a passive delivery device.
Figure 2A:
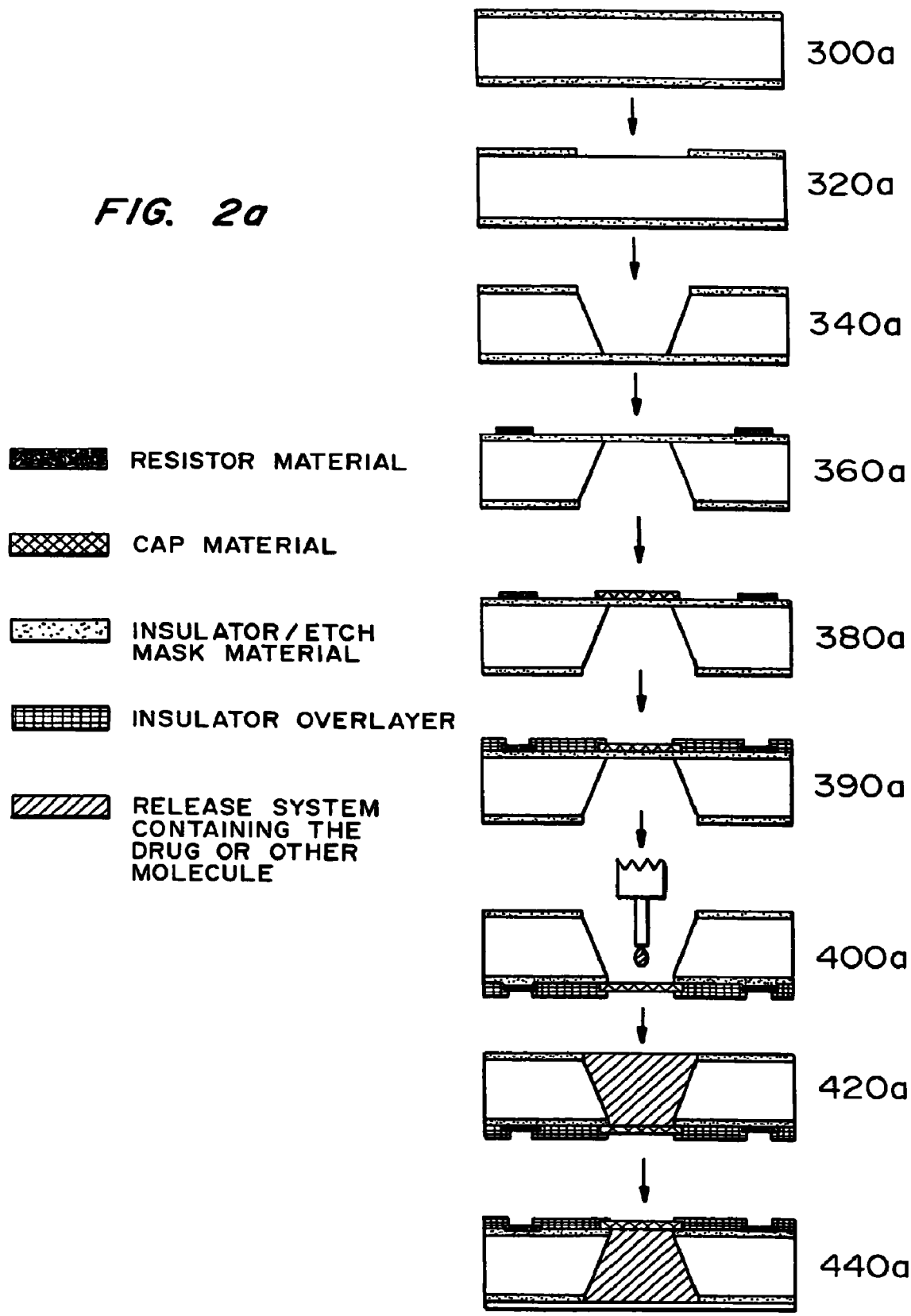
Figure 2B:
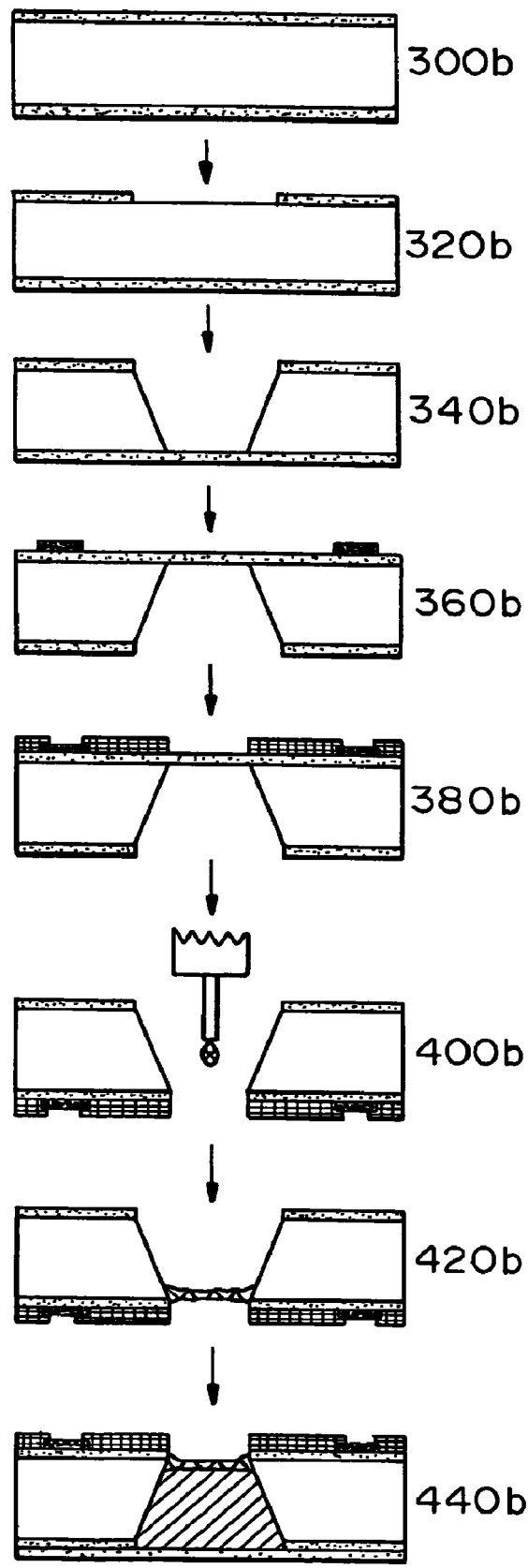

Microchip delivery devices are provided that control both the rate and time of release of molecules, wherein the device includes a substrate, at least one reservoir in the substrate containing the molecules, and a reservoir cap positioned on the reservoir over the molecules, wherein the molecules are released from the reservoir upon heating or cooling the device or a portion thereof sufficient to rupture the reservoir cap.

As used herein, the term "rupture" includes fracture or some other form of mechanical failure, as well as a loss of structural integrity due to a phase change, e.g., melting, in response to a change in temperature, unless a specific one of these mechanisms is indicated.

As used herein, a "microchip" is a miniaturized device fabricated using methods commonly applied to the manufacture of integrated circuits and MEMS (MicroElectroMechanical Systems) such as ultraviolet (UV) photolithography, reactive ion etching, and electron beam evaporation, as described, for example, by Wolf & Tauber, *Silicon Processing for the VLSI Era, Volume 1—Process Technology* (Lattice Press, Sunset Beach, Calif., 1986); and Jaeger, *Introduction to Microelectronic Fabrication*, Volume V in *The Modular Series on Solid State Devices* (Addison-Wesley, Reading, Mass., 1988), as well as MEMS methods that are not standard in making computer chips, including those described, for example, in Madou, *Fundamentals of Microfabrication* (CRC Press, 1997) and micromolding and micromachining techniques known in the art. The microchips provide control over the rate the molecules are released as well as the time at which release begins. The time of release can be controlled passively or actively. The microchip fabrication procedure allows the manufacture of devices with primary dimensions (length of a side if square or rectangular, or diameter if circular) ranging from less than a millimeter to several centimeters. The substrate thickness for a typical device is 500 µm. However, the thickness of the device can vary from approximately 10 µm to several centimeters, depending on the device's application. The substrate may consist of only one material, or may be a composite or multi-laminate material, that is, composed of several layers of the same or different substrate materials that are bonded together. Total device thickness and reservoir volume can be increased by bonding or attaching additional silicon wafers or other substrate materials together to form the microchip device, as shown, for example in FIGS. 6a-d.

In general, changing the device thickness affects the volume of each reservoir and may affect the maximum number of reservoirs that may be incorporated onto a microchip. In vivo applications of the device typically require devices having a primary dimension of 5 cm or smaller. Devices for in vivo applications may be made small enough to be swallowed or implanted using minimally invasive procedures. Smaller in vivo devices (on the order of a millimeter or less) can be implanted using a catheter or other injectable means. Devices for in vitro applications have fewer size restrictions and, if necessary, can be made much larger than the dimension ranges for in vivo devices.

Materials for Device Fabrication

Each device consists of at least of a substrate, reservoirs, and a release system containing, enclosing, or layered with the molecules to be delivered. The device also includes a reservoir cap over each reservoir to control the release time of the molecules. Active devices may further include control circuitry and a power source.

A. The Substrate

The substrate contains the etched, machined, or molded reservoirs and serves as the support for the microchip. Any material which can serve as a support, is suitable for etching, machining, or molding, and is impermeable to the molecules to be delivered and to the surrounding fluids (e.g., water, blood, electrolytes or other solutions) may be used as a substrate. Examples of substrate materials include glasses, ceramics, metals, semiconductors, and degradable and non-degradable polymers. The substrate can be formed of only one material or can be a composite or multi-laminate material, e.g., several layers of the same or different substrate materials that are bonded together. Composite or multi-laminate substrates can include any number of layers of silicon, glasses, ceramics, semiconductors, metals, polymers, and can also be formed of two or more complete microchip devices that have been bonded together (see FIGS. 6a-d). For in vivo applications, biocompatibility of the substrate material is preferred, but not required. For in vivo applications, non-biocompatible materials may be encapsulated in or coated by a biocompatible material, such as poly(ethylene glycol) or polytetrafluoroethylene-like materials, before use. One example of a strong, non-degradable, easily etched substrate that is impermeable to the molecules to be delivered and the surrounding fluids is silicon. One embodiment of a multi-laminate substrate includes bonding silicon and glass together. In another embodiment, the substrate is made of a strong material that degrades or dissolves over a period of time into biocompatible components. This embodiment is preferred for in vivo applications where the device is implanted and physical removal of the device later is not feasible or recommended, for example, brain implants. An example of a class of strong, biocompatible materials are the poly(anhydride-co-imides) described in Uhrich et al., "Synthesis and characterization of degradable poly(anhydride-co-imides)", *Macromolecules,* 28:2184-93 (1995).

B. Release System

The molecules to be delivered may be inserted into the reservoirs in their pure form, as a solid, liquid solution or gel, or as a material that quickly vaporizes. Alternatively, the molecules may be encapsulated within or by a release system. As used herein, "release system" includes both the situation where the molecules (1) are in pure form, as either a solid, liquid, gel or vapor, or (2) are in a matrix formed of degradable material or a material which releases incorporated molecules by diffusion out of or disintegration of the matrix. The molecules can be sometimes contained in a release system because the degradation, dissolution, or diffusion properties of the release system provide a method for controlling the release rate of the molecules. The molecules can be homogeneously or heterogeneously distributed within the release system. Selection of the release system is dependent on the desired rate of release of the molecules. Both non-degradable and degradable release systems can be used for delivery of molecules. Suitable release systems include polymers and polymeric matrices, non-polymeric matrices, or inorganic and organic excipients and diluents such as, but not limited to, calcium carbonate and sugar. Release systems may be natural or synthetic, although synthetic release systems are preferred due to the better characterization of release profiles.

The release system is selected based on the period over which release from a reservoir or group of reservoirs is desired, generally in the range of minutes to days. In some in vivo embodiments, a single device having many reservoirs to release material can provide release for an extended period of time, such as one to twelve months. In contrast, for some in vitro applications, it may be desirable to have release times from a device as short as a few seconds or minutes. In some cases, continuous (constant) release from a reservoir may be most useful. In other cases, a pulse (bulk) release from a reservoir may provide results that are more effective. In one embodiment, single pulses from individual reservoirs can effectively provide a pulsatile release profile by sequentially releasing multiple reservoirs. It is also possible to incorporate several layers of a release system and other materials into a single reservoir to achieve pulsatile delivery from a single reservoir. Continuous release can be achieved by incorporating a release system that degrades, dissolves, or allows diffusion of molecules through it over an extended period of time. In addition, continuous release can be simulated by precisely timing the release of several pulses of molecules in quick succession.

The release system material can be selected so that molecules of various molecular weights are released from a reservoir by diffusion out of or through the material or by degradation of the material. Biodegradable polymers, bioerodible hydrogels, and protein delivery systems are preferred for release of molecules by diffusion, degradation, or dissolution. In general, these materials degrade or dissolve either by enzymatic hydrolysis or exposure to water in vivo or in vitro, or by surface or bulk erosion. Representative synthetic, biodegradable polymers include poly(amides) such as poly(amino acids) and poly(peptides); poly(esters) such as poly(lactic acid), poly(glycolic acid), poly(lactic-co-glycolic acid), and poly(caprolactone); poly(anhydrides); poly(orthoesters); poly(carbonates); and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include poly(ethers) such as poly(ethylene oxide), poly(ethylene glycol), and poly(tetramethylene oxide); vinyl polymers; poly(acrylates) and poly(methacrylates) such as methyl, ethyl, other alkyl, hydroxyethyl methacrylate, acrylic and methacrylic acids, and others such as poly(vinyl alcohol), poly(vinyl pyrolidone), and poly(vinyl acetate); poly(urethanes); cellulose and its derivatives such as alkyl, hydroxyalkyl, ethers, esters, nitrocellulose, and various cellulose acetates; poly(siloxanes); and any chemical derivatives thereof (substitutions, additions of chemical groups, for example, alkyl, alkylene, hydroxylations, oxidations, and other modifications routinely made by those skilled in the art), copolymers and mixtures thereof.

C. Molecules to be Released

Any natural or synthetic, organic or inorganic molecule or mixture thereof can be delivered. In one embodiment, the microchip is used to deliver drugs systemically to a patient in need thereof. In another embodiment, the construction and placement of the microchip in a patient enables the localized release of drugs that may be too potent for systemic delivery. As used herein, drugs are organic or inorganic molecules, including proteins, nucleic acids, polysaccharides and synthetic organic molecules, having a bioactive effect, for example, anesthetics, vaccines, chemotherapeutic agents, hormones, metabolites, sugars, immunomodulators, antioxidants, ion channel regulators, and antibiotics. The drugs can be in the form of a single drug or drug mixtures and can include pharmaceutically acceptable carriers.

In another embodiment, molecules are released in vitro in any system where the controlled release of a small (milligram to nanogram) amount of one or more molecules is required, for example, in the fields of analytic chemistry or medical diagnostics. Molecules can be effective as pH buffering agents, diagnostic agents, and reagents in complex reactions such as the polymerase chain reaction or other nucleic acid amplification procedures.

In still another embodiment, the molecules to be released are perfumes, fragrances, dyes, coloring agents, sweeteners, or a variety of other compounds useful to release, for example, as a function of temperature change.

D. Reservoir Caps

Figure 10A:
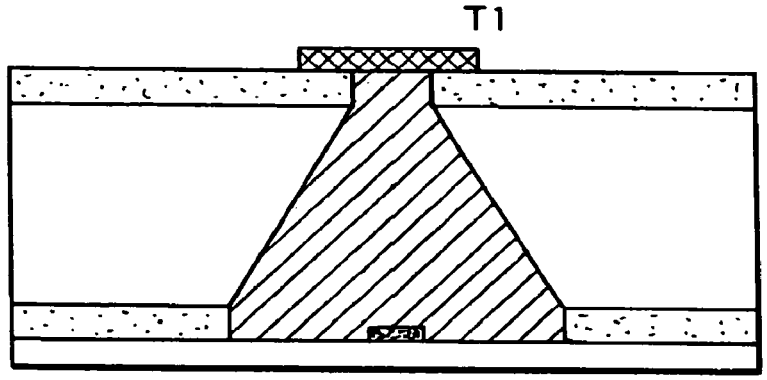
FIGS. 10a-c are cross-sectional schematic views of molecular release via cap fracture due to the expansion of the release system.
Figure 10B:
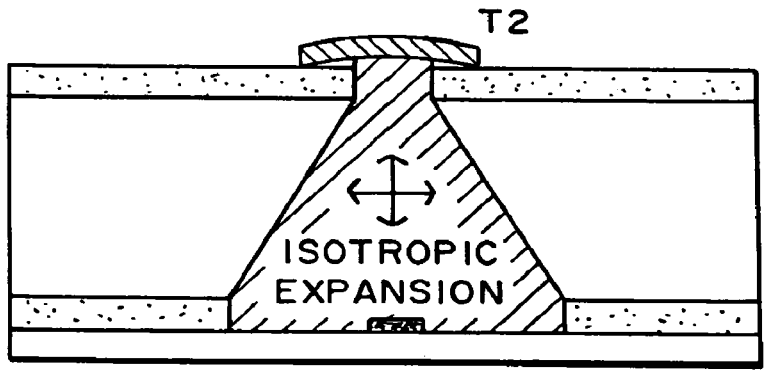
Figure 10C:
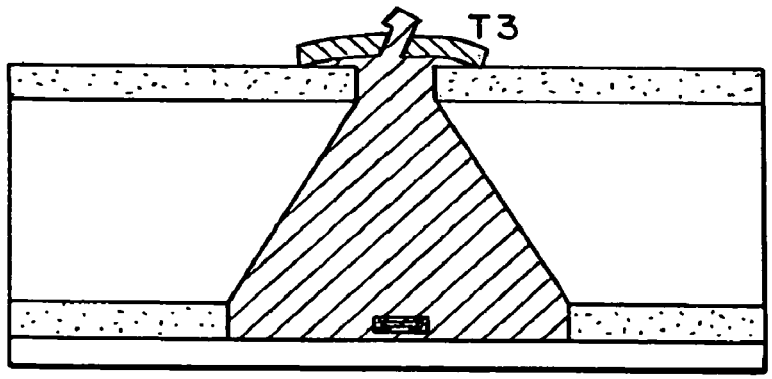
Figure 11A:
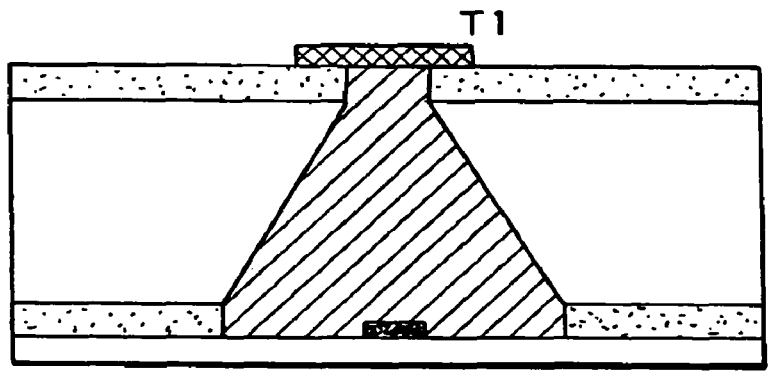
FIGS. 11a-c are cross-sectional schematic views of molecular release via cap fracture due to vapor pressurization.
Figure 11B:
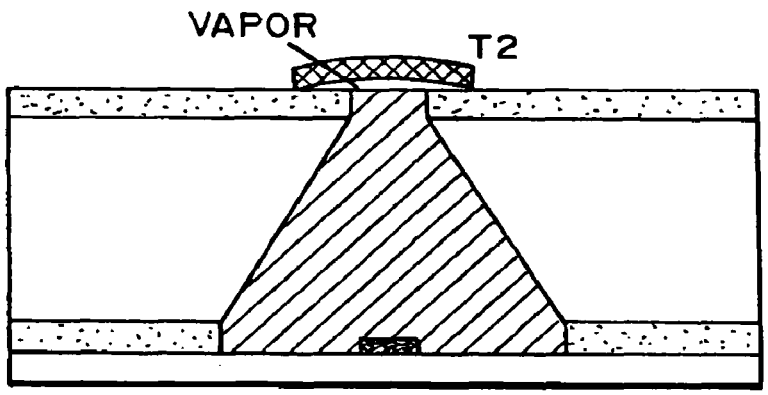
Figure 11C:
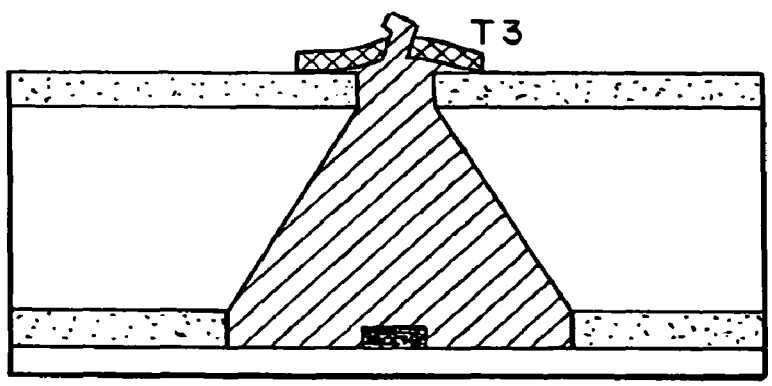

The reservoir cap is positioned on the reservoir over the molecules, which are released from the reservoir upon heating or cooling the device, or a portion thereof, to rupture the reservoir cap. In a preferred embodiment, which is shown schematically in FIG. 10, the heating or cooling causes the molecules in the reservoir to thermally expand (i.e., increase in volume). At a given temperature (T1), the release system completely fills the volume of the reservoir (FIG. 10a). Upon heating to temperature T2 (FIG. 10b), the release system begins to expand and applies a force on the reservoir cap. Once this force exceeds the fracture strength of the cap (FIG. 10c), the cap fractures and the molecules are released. In a variation of this embodiment, which is shown in FIG. 11, the molecules can vaporize or undergo a reaction, thereby elevating the pressure within the reservoir sufficiently to cause the reservoir cap to rupture due to the mechanical stress. Prior to the application of heat (FIG. 11a), the pressure within the reservoir is lower than that needed to rupture the reservoir cap. The addition of heat increases the equilibrium pressure within the reservoir (FIG. 11b) and the forces acting on the cap material increase. Further increases in temperature cause the pressure to continue to increase until the internal pressure overcomes the fracture strength of the reservoir cap (FIG. 11c). Typically, the thermal expansion, vaporization, or reaction is induced by heating the molecules in the reservoir, e.g., above ambient temperatures. In certain applications, however, the thermal expansion or reaction can be induced by cooling the molecules in the reservoir. Water, for example, expands upon freezing. If a material that thermally contracts upon cooling is used as the reservoir cap over aqueous molecules, then the mechanical failure should be further enhanced by sufficient cooling.

Figure 12A:
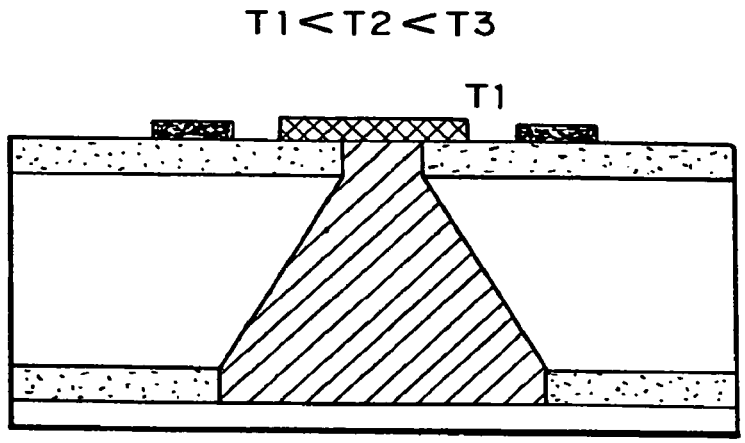
FIGS. 12a-c are cross-sectional schematic views of molecular release via cap fracture due to cap expansion.
Figure 12B:
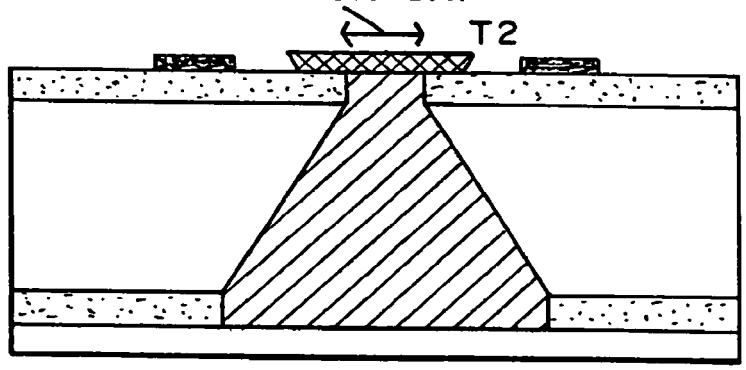
Figure 12C:
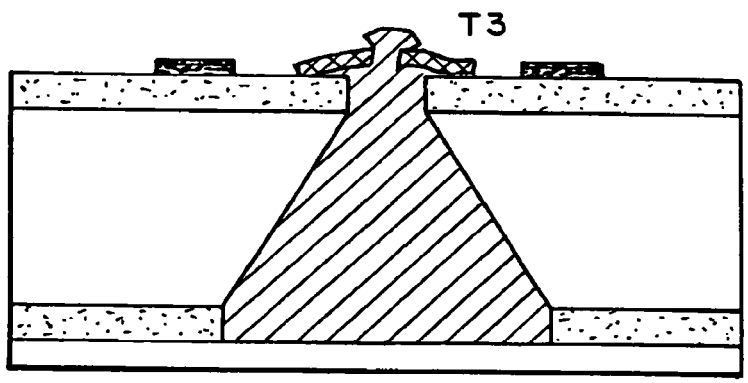

In one embodiment, the reservoir cap is ruptured by physical (i.e., structural) or chemical changes in the reservoir cap material itself, for example, a change caused by a temperature change. For example, the reservoir cap can be made of or include a material that expands when heated. When the reservoir cap is secured in a fixed position and heated (FIG. 12b), the reservoir cap expands until it cracks or ruptures due to the increase in volume (FIG. 12c). This embodiment permits heating of the reservoir cap with minimal or no heating of the reservoir contents, a feature that is particularly important when the reservoir contains heat-sensitive molecules, such as protein drugs, which can denature upon exposure to excessive heat.

Figure 13A:
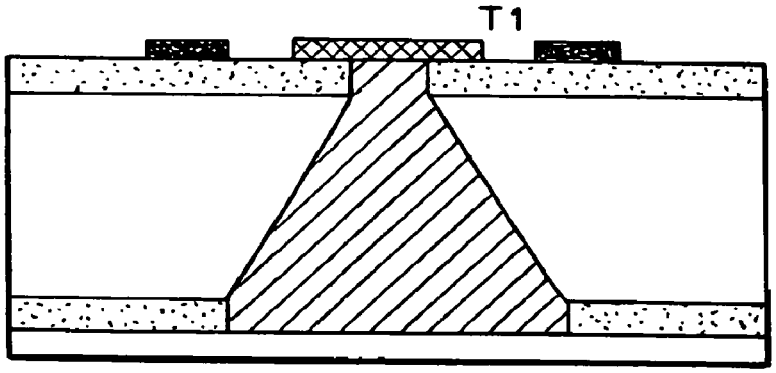
FIGS. 13a-c are cross-sectional schematic views of molecular release by melting (i.e., phase change) of the cap.
Figure 13B:
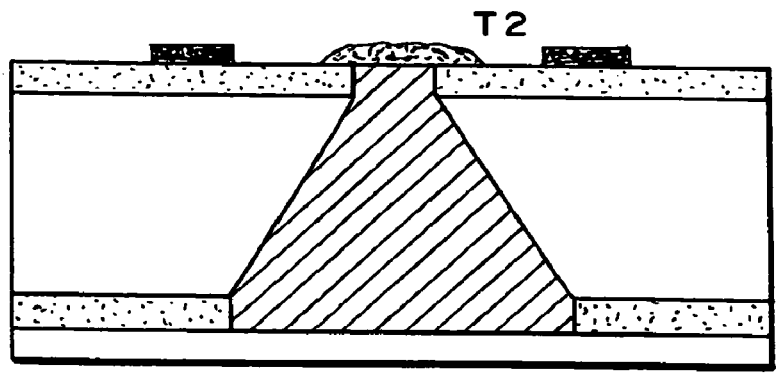
Figure 13C:
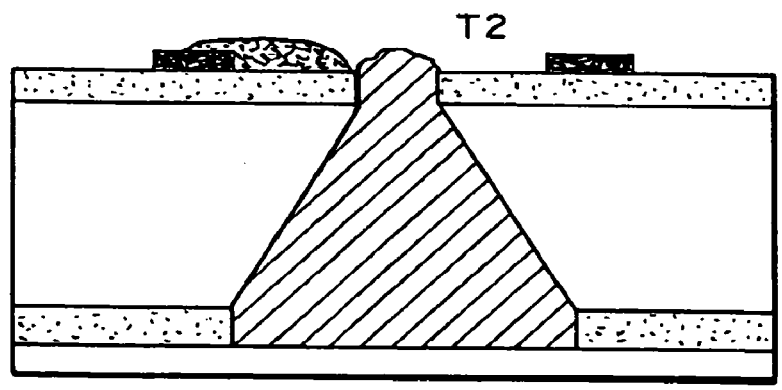

In another embodiment using an active release mechanism, the reservoir cap material is melted (i.e., undergoes a phase change) using resistive heating. For in vivo applications, the reservoir cap preferably is composed of biocompatible copolymers, such as organic hydroxy acid derivatives (e.g., lactides and lactones), which can offer a range of selectable melting temperatures (see PCT WO 98/26814). Particular melting temperatures, for example between about 2° C. and about 12° C. above normal body temperature, can be selected for the reservoir caps by proper selection of starting monomer ratios and the resulting molecular weight of the copolymer. This type of reservoir opening mechanism offers at least two delivery schemes. A first scheme is based on individual reservoir caps having various melting temperatures. By heating the device, or portion thereof, to a constant temperature, only specific reservoir caps melt, opening the reservoir and exposing the molecules. The application of different temperature profiles therefore provides for the selective molecular release. A second scheme, shown in FIG. 13, focuses on all caps having a fixed composition and a uniform melting temperature. The cap is a solid phase at temperature T1 (FIG. 13a). Locally heating individual reservoir caps to temperature T2 (FIG. 13b) causes the reservoir cap to become molten. The fluidized reservoir cap is then mobile, which facilitates the opening of the reservoir and release of molecules (FIG. 13c). In the case of in vitro applications, similar active schemes are possible with less stringent compositional and temperature requirements.

In the passive release embodiments, reservoir cap rupture is triggered by environmental temperature changes, for example, due to the placement of the device onto or into the body of a human or other animal. The passive mechanism differs from the active mechanism in that rupture of the reservoir cap of the active device is triggered by a directly applied temperature change rather than an environmental one.

In one embodiment of passive devices, the reservoir cap is thermally stimulated to enhance degradation. For example, the kinetics of reservoir cap degradation can be very slow at room temperature and the cap can be considered chemically stable. However, the kinetics of degradation are significantly increased by increasing the temperature of the cap material, e.g., by in vivo implantation. The absolute rate of degradation can be selected by controlling the composition of the reservoir cap material. For example, the degradation rate of biocompatible copolymers (e.g., lactones and lactides) can be between several hours and several years, preferably between 2 days and 1 year at a temperature of 37° C., depending on the specific molar ratios of the primary structural units. By using an array of reservoir caps, each having a different composition, complex molecular release profiles can be achieved once the device 20 reaches a critical temperature defined by its environment.

In another embodiment of passive devices, all reservoir caps have constant disintegration rates (e.g., temperature independent) and the release profile is controlled by selection of the physical dimensions of the reservoir cap material. By fixing the rate of disintegration, the time for cap disintegration is dependent on the thickness of the reservoir cap material. For example, in an embodiment in which all reservoir caps have identical compositions, molecular release can be controlled by varying the thickness of the cap.

In both the active and passive devices, the reservoir cap is formed of a material having a yield or tensile strength beyond which the material fails by fracture or a material that undergoes a phase change (for example, melts) with selected changes in temperature. The material preferably is selected from metals, such as copper, gold, silver, platinum, and zinc; glasses; ceramics; semiconductors; and brittle polymers, such as semicrystalline polyesters. Preferably, the reservoir cap is in the form of a thin film, e.g., a film having a thickness between about 0.1 µm and 1 µm. However, because the thickness depends on the particular material and the mechanism of rupture (i.e., electrochemical vs. mechanical breakdown), thicker reservoir caps, e.g., having a thickness between 1 µm and 100 µm or more, may work better for some materials, such as certain brittle material.

The reservoir cap optionally can be coated with an overcoat material to structurally reinforce the rupturable material layer until the overcoat material has been substantially removed by dissolving, eroding, biodegrading, oxidizing, or otherwise degrading, such as upon exposure to water in vivo or in vitro. Representative suitable degradable materials include synthetic or natural biodegradable polymers.

Reservoir caps in either passive or active embodiments can be formed of a material that functions as a permeable or semi-permeable membrane depending on the temperature. Examples of such caps are described further in Example 2 below.

E. Resistors for Heating

In a preferred embodiment of the active device, a resistor is integrated into the reservoir or mounted near the reservoir, which upon application of an electric current through the resistor, heats the contents of the reservoir, the cap material, or both. In typical embodiments, resistors are located at the bottom or along the inside walls of the reservoirs, or they may be located on or near the reservoir caps covering the small reservoir openings. The resistor generally is a thin-film resistor, which can be integrated with the reservoir during the manufacturing process. Such resistors can be made of metals such as platinum or gold, ceramics, semiconductors, and some polymers. Methods for fabricating these resistors are described, for example, in Wogersien et al. "Fabrication of Thin Film Resistors and Silicon Microstructures Using a Frequency Doubled Nd:YAG-Laser," *Proc. SPIE—Int. Soc. Opt. Eng.*, 3680:1105-12 (1999); Bhattacharya & Tummala, "Next Generation Integral Passives: Materials, Processes, and Integration of Resistors and Capacitors on PWB Substrates," *J. Mater. Sci.-Mater. Electron.* 11(3):253-68 (2000); and Vladimirsky et al., "Thin Metal Film Thermal Microsensors," *Proc. SPIE-Int. Soc. Opt. Eng.*, 2640:184-92 (1995). Alternatively, small chip resistors can be surface mounted on the device in close proximity to the reservoir or reservoir cap.

Figure 9A:
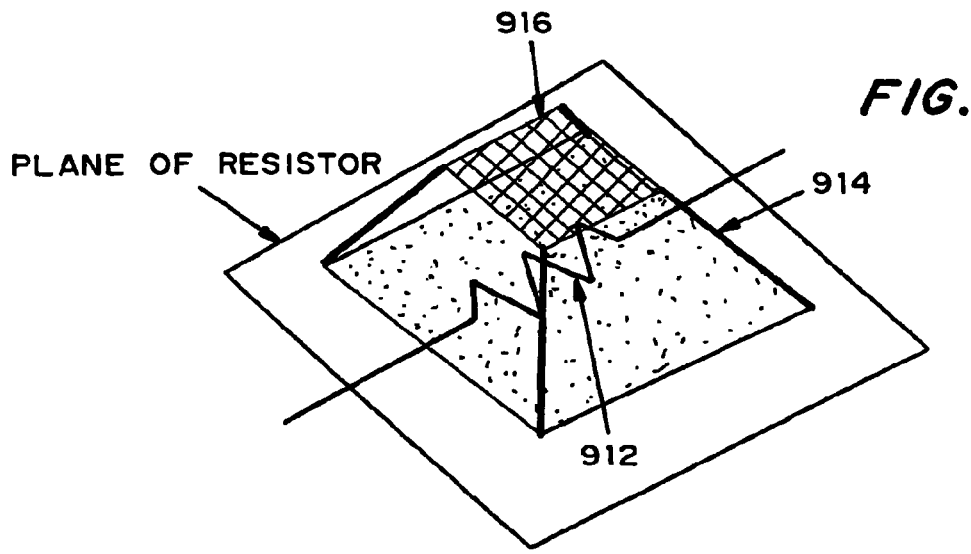
FIGS. 9a-c are perspective schematic views of configurations of thermally-activated chemical delivery devices.
Figure 9B:
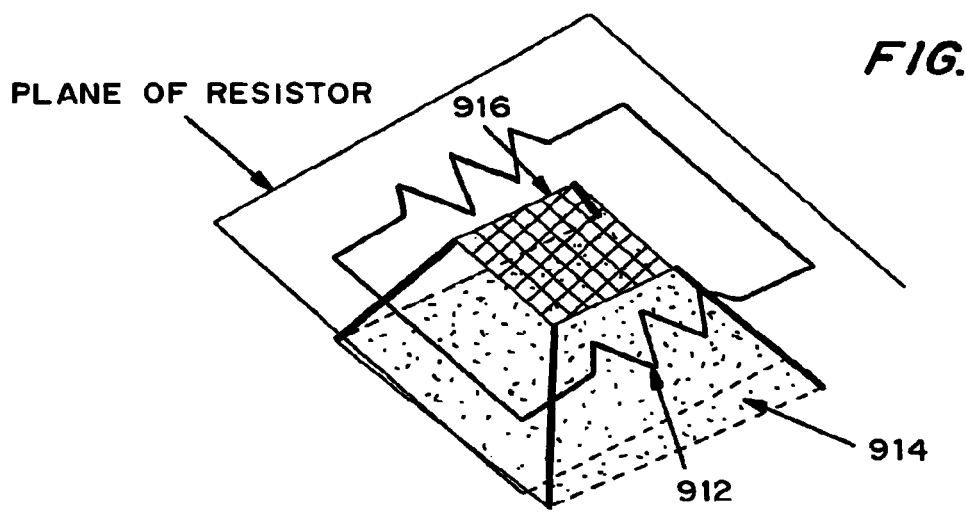
Figure 9C:
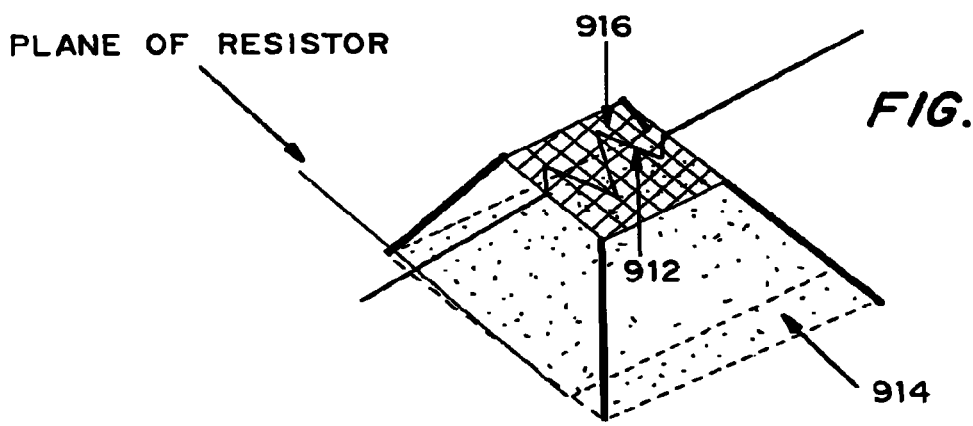

FIGS. 9a-c illustrate three possible configurations of reservoirs, reservoir caps, and associated resistors. The substrate is not shown in these Figures. FIG. 9a shows resistor 912 in the bottom of the reservoir 914 which is covered by reservoir cap 916, such that the plane in which the resistors exist is substantially along the bottom of the reservoir. FIG. 9b shows resistor 912 near the top of reservoir cap 916 covering reservoir 914, and FIG. 9c shows resistor 912 on top of or just below reservoir cap 916 covering reservoir 914. The plane in which the resistors exist in these two configurations is substantially along the top, or just above the top, of the reservoir.

F. Device Packaging, Control Circuitry, and Power Source

Microelectronic device packages are typically made of an insulating or dielectric material such as aluminum oxide or silicon nitride. Their purpose is to allow all components of the device to be placed in close proximity and to facilitate the interconnection of components to power sources and to each other. Some potential types of packages include multi-chip modules (MCM's) or hybrid packages. For in vivo applications of the delivery device, the entire package, including all components (i.e., the device, the microprocessor, and the power source), are coated or encapsulated in a biocompatible material such as poly(ethylene glycol) or polytetrafluoroethylene-like materials. The materials requirements for in vitro applications may be less stringent and depend on the particular situation.

The control circuitry consists of a timer, a demultiplexer, a microprocessor, and an input source, for example, a memory source, a signal receiver, or a biosensor. The timer and demultiplexer circuitry can be designed and incorporated directly onto the surface of the microchip during electrode fabrication, or may consist of pre-fabricated components integrated into the microchip package. The criteria for selection of a microprocessor are small size, low power requirement, and the ability to translate the output from memory sources, signal receivers, or biosensors into an address for the direction of power through the demultiplexer to a specific reservoir on the delivery device. Selection of a source of input to the microprocessor such as memory sources, signal receivers, or biosensors depends on the delivery device's particular application and whether device operation is preprogrammed, controlled by remote means, or controlled by feedback from its environment (i.e., biofeedback).

The criteria for selection of a power source are small size, sufficient power capacity, ability to be integrated into the control circuitry or the package, the ability to be recharged, and the length of time before recharging is necessary. Several lithium-based, rechargeable microbatteries have been described in Jones & Akridge, "Development and performance of a rechargeable thin-film solid-state microbattery", *J. Power Sources,* 54:63-67 (1995); and Bates et al., "New amorphous thin-film lithium electrolyte and rechargeable microbattery", *IEEE 35$^{th}$ International Power Sources Symposium,* pp. 337-39 (1992). These batteries are typically only ten microns thick and occupy 1 cm$^2$ of area. One or more of these batteries can be incorporated directly onto the delivery device or package.

Methods of Microchip Device Fabrication

Methods for fabricating the microchip devices are described herein. These techniques are adapted from techniques described in U.S. Pat. No. 5,797,898 and U.S. Pat. No. 6,123,861, which are herein incorporated by reference.

Preferred methods of making passive and active devices are shown in FIG. 1 and FIGS. 2*a-d*, respectively. These methods are described in the following text and in Examples 1-3. Although the fabrication methods described in the Examples use microfabrication and microelectronic processing techniques, it is understood that fabrication of any active and passive microchip chemical delivery devices is not limited to materials such as semiconductors or processes typically used in microelectronics manufacturing. For example, other materials, such as metals, ceramics, and polymers, can be used in the devices. Similarly, other fabrication processes, such as plating, casting, or molding, can also be used to make them.

A. Fabrication of the Reservoirs

Devices are manufactured by adapting techniques known to those skilled in the art, which are reviewed, for example, by Wolf et al. (1986), Jaeger (1988), and Madou, *Fundamentals of Microfabrication* (CRC Press, 1997)

Fabrication begins by depositing and photolithographically patterning a material, typically an insulating or dielectric material, onto the substrate to serve as an etch mask during reservoir etching. Typical insulating materials for use as a mask include silicon nitride, silicon dioxide, and some polymers, such as polyimide. In a preferred embodiment, a thin film (approximately 1000-3000 Å) of low stress, silicon-rich nitride is deposited on both sides of a silicon wafer in a Vertical Tube Reactor (VTR). Alternatively, a stoichiometric, polycrystalline silicon nitride ($Si_3N_4$) can be deposited by Low Pressure Chemical Vapor Deposition (LPCVD), or amorphous silicon nitride can be deposited by Plasma Enhanced Chemical Vapor Deposition (PECVD). Reservoirs are patterned into the silicon nitride film on one side of the wafer by ultraviolet photolithography and either plasma etching processes (i.e., reactive ion etching) or a chemical etch consisting of hot phosphoric acid or buffered hydrofluoric acid. The patterned silicon nitride serves as an etch mask for the chemical etching of the exposed silicon 34/340 by a concentrated potassium hydroxide solution (approximately 20-40% KOH by weight at a temperature of 75-90° C.). Alternatively, the reservoirs can be etched into the substrate by TMAH (tetra-methyl ammonium hydroxide) or by dry etching techniques such as reactive ion etching or ion beam etching. These techniques are commonly used in the fabrication of microelectronic or MEMS (MicroElectroMechanical Systems) devices, as reviewed, for example, by Wolf et al. (1986), Jaeger (1988), and Madou (1997). Use of these microfabrication techniques allows the incorporation of hundreds to thousands of reservoirs on a single microchip. The spacing between each reservoir depends on its particular application and whether the device is a passive or active device. In a passive device, the reservoirs may be less than one micron apart. In an active device, the distance between the reservoirs may be slightly larger (between approximately 1 and 10 µm) due to the space occupied by the resistors or other electrical elements on or near each reservoir. Reservoirs can be made in nearly any shape and depth, and need not pass completely through the substrate. In a preferred embodiment, the reservoirs are etched into a (100) oriented, silicon substrate by potassium hydroxide, in the shape of a square pyramid having side walls sloped at 54.7°, and pass completely through the substrate (for example, 500 µm thick) to the silicon nitride film on the other side of the substrate, forming a silicon nitride membrane. (Here, the silicon nitride film serves as a potassium hydroxide etch stop.) The pyramidal shape allows easy filling of the reservoirs through the large opening of the reservoir (example dimensions are 800 µm by 800 µm) on the patterned side of the substrate, release through the small opening of the reservoir (example dimensions are 50 µm by 50 µm) on the other side of the substrate, and provides a large cavity inside the device for storing the drugs or other molecules to be delivered.

B. Fabrication of Resistors

In a preferred embodiment of the active devices, resistors are integrated into the device. Typically, thin-film resistors are located at the bottom or along the inside walls of the reservoirs, or they may be located on or near the reservoir caps covering the small reservoir openings. These resistors are fabricated using photolithography and thin film deposition techniques, as described herein and known to those skilled in the art. Alternatively, small chip resistors can be surface mounted inside or in close proximity to the reservoir.

C. Fabrication of Passive Timed Release Reservoir Caps

In FIG. 1, the steps represented by 36*a*, 38*a*, and 40*a*, are conducted using ink jet or microinjection, while the steps represented by 36*b*, 38*b*, and 40*b*, are conducted using spin coating. In the fabrication of passive timed release microchips, the reservoir cap material is injected with a microsyringe 36*a*, printed with an inkjet printer cartridge, or spin coated 36*b* into a reservoir having the thin membrane of insulating mask material still present over the small opening of the reservoir. Alternatively, the reservoir cap material can be injected into reservoirs that no longer have the insulating mask material covering the small opening of the reservoir. Depending on the nature of the cap material, capillary forces and surface tension can form an unsupported membrane of the cap material at the small reservoir opening. The cap material can be in liquid form, or may dry to form a solid or semi-solid cap over the small reservoir opening. In either case, if injection or inkjet printing methods are used, cap formation is complete after the material is injected or printed into the reservoir 38a and does not require further processing. If spin coating is used, the cap material is planarized by multiple spin coatings 36b. The surface of the film is then etched by a plasma, an ion beam, or chemical etchant until the desired cap thickness is obtained 38b. In a preferred embodiment, the insulating material used is silicon nitride and the cap material is injected into the reservoir with a microinjector filled with a solution or suspension of the cap material.

Reservoir caps control the time at which molecules are released from the reservoirs. Each reservoir cap can have different physical or thermal properties to vary the time at which each release system containing the molecules is exposed to the surrounding fluids. For example, reservoir caps having different compositions may degrade, dissolve, or disintegrate at different rates and times when the device is exposed to a particular temperature, either higher or lower than room temperature (which is generally considered to be about 20-25° C.).

In one embodiment, reservoir caps are made by filling the release end of the reservoir with reservoir cap material, for example by injection, inkjet printing, or spin coating. Injection and inkjet printing are the preferred methods of filling deep (greater than 10 μm) reservoirs or reservoirs with large openings (greater than 50 μm). For example, to obtain different cap thicknesses using injection or inkjet printing, different amounts of cap material are injected or printed directly into each individual reservoir. Spin coating is the preferred method of filling shallow (less than 10 μm) reservoirs, reservoirs that do not pass completely through the substrate, or reservoirs with small (less than 50 μm) openings. Variation in reservoir cap thickness or material by spin coating can be achieved by a repeated, step-wise process of spin coating, masking selected reservoirs, and etching. For example, to vary cap thickness with spin coating, the cap material is spin coated over the entire substrate. Spin coating is repeated, if necessary, until the material is nearly planarized. A mask material such as photoresist is patterned to cover the cap material in all the reservoirs except one. Plasma, ion beam, or chemical etchants are used to etch the cap material in the exposed reservoir to the desired thickness. The photoresist is then removed from the substrate. The process is repeated as a new layer of photoresist is deposited and patterned to cover the cap material in all the reservoirs except one (the exposed reservoir is not the same one already etched to its desired thickness). Etching of the exposed cap material in this reservoir continues until the desired cap thickness is obtained. This process of depositing and patterning a mask material such as photoresist, etching, and mask removal can be repeated until each reservoir has its own unique cap thickness. The techniques (e.g., UV photolithography and plasma or ion beam etching) are well known to those skilled in the field of microfabrication.

Although injection, inkjet printing and spin coating are the preferred methods of reservoir cap fabrication, it is understood that each reservoir can be capped individually by capillary action, surface tension, by pulling or pushing the material into the reservoir using a vacuum or other pressure gradient, by melting the material into the reservoir, by centrifugation and related processes, by manually packing solids into the reservoir, or by any combination of these or similar reservoir filling techniques.

Once a cap fabrication method is selected, additional methods for controlling the time of release of molecules from a reservoir can be utilized, for example, by including temperature sensitive polymers or UV polymerizable polymers, or by the layering of release system and cap materials. In the first embodiment, the composition of reservoir caps comprised of temperature sensitive polymers can control the time and rate at which the caps degrade, dissolve, or disintegrate at a particular temperature (e.g., body temperature). For example, the kinetics of reservoir cap degradation can be very slow at room temperature and the cap can be considered chemically stable. However, the kinetics of degradation are significantly increased by increasing the temperature of the cap material, e.g., by in vivo implantation. The absolute rate of degradation can be selected by controlling the composition of the reservoir cap material. For example, the degradation rate of biocompatible copolymers (e.g., lactones and lactides) can be between several hours and several years at a temperature of 37° C., depending on the specific molar ratios of the primary structural units. By using an array of reservoir caps, each having a different composition, complex molecular release profiles can be achieved once the device reaches a critical temperature defined by its environment. In a second embodiment, the reservoir caps are made of either an injected, inkjet printed or spin coated UV polymerizable polymer, each cap can be exposed to a different intensity of UV light to give varying degrees of crosslinking and therefore, different temperature dependent degradation or dissolution rates for degradable caps or different permeabilities to the molecules for non-degradable caps. In a third embodiment, polymers that possess diffusion properties affected by temperature can be used as a cap material. For example, polymers having different glass transition temperatures can be used to affect the release rate at a given temperature. This technique is possible where chemical diffusion rates through the polymer vary with the proximity of the polymer's current temperature to its glass transition temperature. Each reservoir cap can be made with a polymer having a different composition, so that at a particular temperature, the reservoir caps have different permeabilities due to their proximity to their glass transition temperature. In a fourth embodiment, layers of cap material, both degradable and non-degradable, can be inserted between layers of the release system containing the molecules to be delivered by injection, inkjet printing, spin coating, or selective crosslinking. These and other similar methods allow complex release profiles (e.g., pulsatile delivery at irregular time intervals) to be achieved from a single reservoir.

If desired, a passive timed release device can be fabricated without reservoir caps. The rate of release of the molecules is thus solely controlled by the physical and material properties of the release system containing the molecule to be delivered.

D. Fabrication of Active Timed Release Reservoir Caps

In a preferred embodiment, photoresist is patterned in the form of reservoir caps on the surface of the substrate having the reservoirs covered by the thin membrane of insulating or dielectric material. The photoresist is developed such that the area directly over the covered opening of the reservoir is left uncovered by photoresist and is in the shape of a reservoir cap. A thin film of material is deposited on the substrate by methods such as evaporation, sputtering, chemical vapor deposition, solvent casting, slip casting, contact printing, spin coating, or other thin film deposition techniques known in the art. After film deposition, the photoresist is stripped from the substrate. This removes the deposited film, except in those areas not covered by photoresist (lift-off technique). This leaves material on the surface of the substrate in the form of reservoir caps. An alternative method involves depositing the material over the entire surface of the device, patterning photoresist on top of the thin film using UV or infrared (IR) photolithography, so that the photoresist lies over the reservoirs in the shape of reservoir caps, and etching the unmasked material using plasma, ion beam, or chemical etching techniques. The photoresist is then stripped, leaving thin film caps covering the reservoirs. Typical film thickness of the reservoir cap material is between 0.05 µm and several microns.

Resistors of various shapes and sizes are fabricated inside the reservoirs or near the reservoir caps using the same photolithography, deposition, and etching methods described in the previous paragraph and known in the art. Thin film resistors are used to selectively apply heat to the molecules in the reservoir or to the reservoir caps and may include one or more types of materials including metals such as platinum or gold, ceramics, semiconductors, and some polymers.

In some embodiments, an insulating or dielectric material such as silicon oxide ($SiO_x$) or silicon nitride ($SiN_x$) is deposited over the entire surface of the device by methods such as chemical vapor deposition (CVD), electron or ion beam evaporation, sputtering, or spin coating. Photoresist is patterned on top of the dielectric to protect it from etching except on the reservoir caps covering each reservoir. The dielectric material can be etched by plasma, ion beam, or chemical etching techniques. The purpose of this film is to protect the resistors from corrosion, degradation, or dissolution in all areas where the resistors do not have to be exposed to the surrounding environment.

In one embodiment, the resistors are positioned in the reservoir in such a way that when an electric current is applied to the resistors, the material in the reservoir expands, contracts, vaporizes, or undergoes a reaction that causes the pressure in the reservoir to increase until the reservoir cap ruptures. In another embodiment, the resistors are positioned near the reservoir caps in such a way that when an electric current is applied to the resistors, the reservoir cap ruptures due to expansion or contraction, or undergoes a phase change that causes it to lose its structural integrity. Once a reservoir is opened, the molecules are released from the reservoir at a rate dependent upon the degradation or dissolution rate of a degradable release system or the rate of diffusion of the molecules out of or through a non-degradable release system.

E. Removal of the Insulator Membrane (Reservoir Etch Stop)

The thin membrane of insulating or dielectric material covering the reservoir used as a mask and an etch stop during reservoir fabrication must be removed from the active timed release device before reservoir filling and from the passive timed release device (if the reservoir extends completely through the substrate) after reservoir filling. The membrane may be removed in two ways. First, the membrane can be removed by an ion beam or reactive ion plasma. In a preferred embodiment, the silicon nitride used as the insulating material can be removed by a reactive ion plasma composed of oxygen and fluorine containing gases such as $CHF_3$, $CF_4$, or $SF_6$. Second, the membrane can be removed by chemical etching. For example, buffered hydrofluoric acid (BHF or BOE) can be used to etch silicon dioxide and hot phosphoric acid can be used to etch silicon nitride.

F. Reservoir Filling

The release system containing the molecules for delivery is inserted into the large opening of the reservoir by injection, inkjet printing, or spin coating. Each reservoir can contain a different molecule and dosage. Similarly, the release kinetics of the molecule in each reservoir can be varied by the choice of the release system and cap materials. In addition, the mixing or layering of release system and cap materials in each reservoir can be used to tailor the release kinetics to the needs of a particular application.

The distribution over the microchip of reservoirs filled with the release system containing the molecules to be delivered can vary depending on the medical needs of the patient or other requirements of the system. For applications in drug delivery, for example, the drugs in each of the rows can differ from each other. One row may contain a hormone and another row may contain a metabolite. In addition, the release system can differ within each row to release a drug at a high rate from one reservoir and a slow rate from another reservoir. The dosages can also vary within each row. For those devices having deep (greater than 10 µm) reservoirs or reservoirs with large (greater than 50 µm) openings, differences in reservoir loading can be achieved by injection or inkjet printing of different amounts of material directly into each reservoir. Variation between reservoirs is achieved in devices having shallow (less than 10 µm) reservoirs, reservoirs that do not pass completely through the substrate, or reservoirs with small (less than 50 µm) openings by a repeated, step-wise process of masking selected reservoirs, spin coating, and etching, as described above regarding the fabrication by spin coating of passive timed release reservoir caps. Preferably, the release system and molecules to be delivered are mixed before application to the reservoirs. Although injection, inkjet printing and spin coating are the preferred methods of filling reservoirs, it is understood that each reservoir can be filled individually by capillary action, surface tension, by pulling or pushing the material into the reservoir using a vacuum or other pressure gradient, by melting the material into the reservoir, by centrifugation and related processes, by manually packing solids into the reservoir, or by any combination of these or similar reservoir filling techniques.

In preferred embodiments of both active and passive release devices, the reservoir openings used for filling (i.e., the openings opposite the reservoir cap end) are sealed following reservoir filling, using any of a variety of techniques known in the art. For example, sealing can be provided by bonding a rigid backing plate or a thin flexible film across the opening. Alternatively, the opening can be sealed by applying a fluid material, e.g., an adhesive, which plugs the opening and hardens to form a seal. In another embodiment, a second substrate portion, e.g., of a second device, can be bonded across the reservoir openings, as shown in FIG. 6.

G. Device Packaging, Control Circuitry, and Power Source

The openings through which the reservoirs of passive and active devices are filled are sealed by wafer bonding or with a waterproof epoxy or other appropriate material impervious to the surrounding fluids. For in vitro applications, the entire unit, except for the face of the device containing the reservoirs and electrodes, is encased in a material appropriate for the system. For in vivo applications, the unit is preferably encapsulated in a biocompatible material such as poly(ethylene glycol) or polytetrafluoroethylene.

Figure 3:
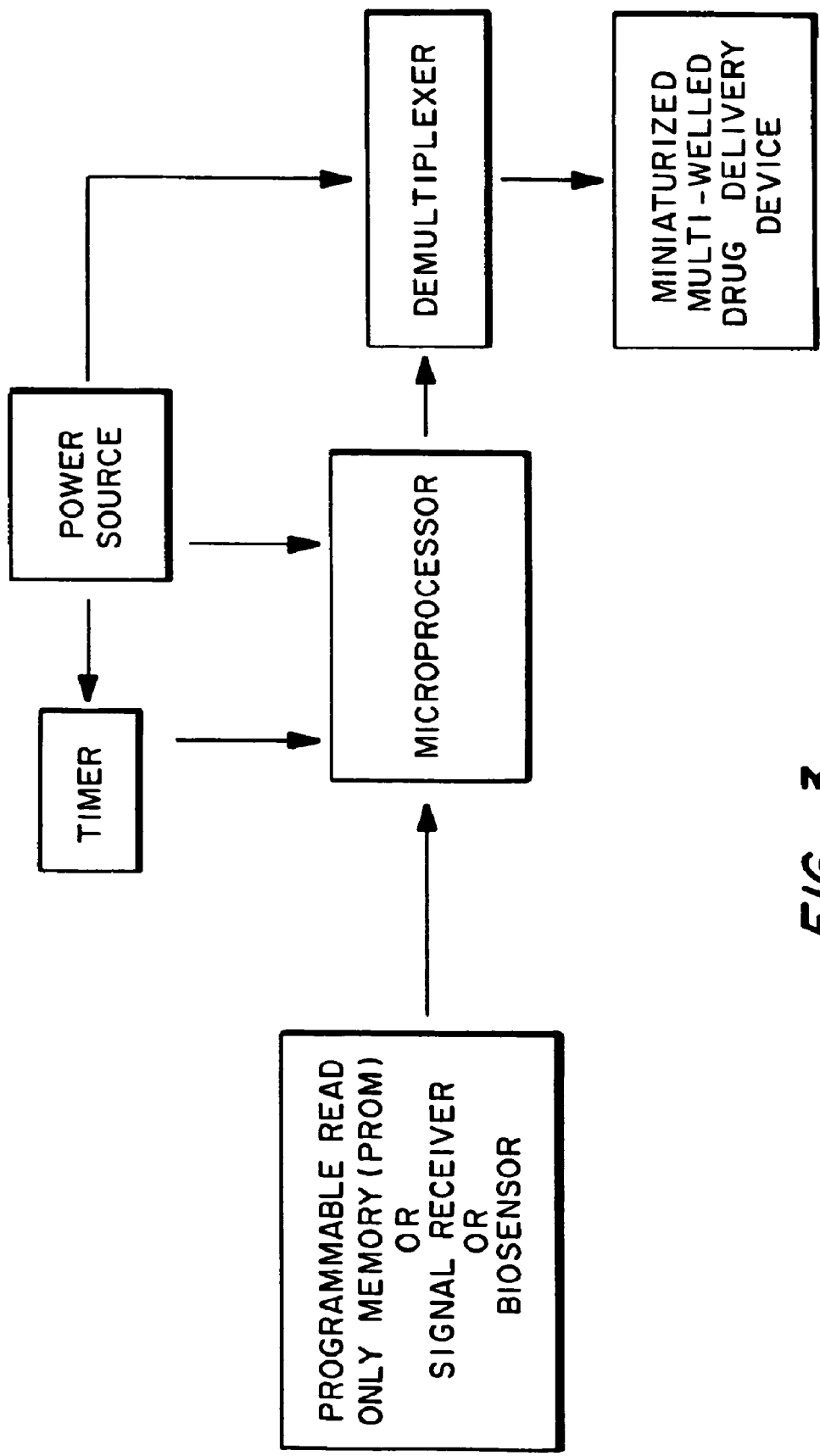
FIG. 3 depicts a typical device control circuitry flowsheet.

The mechanism for release of molecules by the active timed release device does not depend on multiple parts fitted or glued together which must retract or dislodge. Control of the time of release of each reservoir can be achieved by a preprogrammed microprocessor, by remote control, by a signal from a biosensor, or by any combination of these methods, as shown schematically in FIG. 3. First, a microprocessor is used in conjunction with a source of memory such as programmable read only memory (PROM), a timer, a demultiplexer, and a power source such as a microbattery, such as is described, for example, by Jones et al. (1995) and Bates et al. (1992). The release pattern is written directly into the PROM by the user. The PROM sends these instructions to the microprocessor. When the time for release has been reached as indicated by the timer, the microprocessor sends a signal corresponding to the address (location) of a particular reservoir to the demultiplexer. The demultiplexer sends an input, such as an electric potential or current, to the reservoir addressed by the microprocessor. A microbattery provides the power to operate the PROM, timer, and microprocessor, and provides the electric potential or current input that is directed to a particular reservoir by the demultiplexer. The manufacture, size, and location of each of these components is dependent upon the requirements of a particular application. In one embodiment, the memory, timer, microprocessor, and demultiplexer circuitry is integrated directly onto the surface of the chip. The microbattery is attached to the other side of the chip and is connected to the device circuitry by vias or thin wires. However, in many cases, it may be preferable to use separate, prefabricated, component chips for memory, timing, processing, and demultiplexing. These components can be integrated with the chemical delivery microchip in a package such as a multi-chip module (MCM) or hybrid package, or they can be attached to the backside of the miniaturized delivery device with the battery. The size and type of prefabricated chips used depends on the overall dimensions of the delivery device and the number of reservoirs. Second, activation of a particular reservoir by the application of an electric current to the resistors can be controlled externally by remote control. Much of the circuitry used for remote control is the same as that used in the preprogrammed method. The main difference is that the PROM is replaced by a signal receiver. A signal such as radio waves, microwaves, low power laser, or ultrasound is sent to the receiver by an external source, for example, computers or ultrasound generators. The signal is sent to the microprocessor where it is translated into a reservoir address. Power is then directed through the demultiplexer to the reservoir having the appropriate address. Third, a biosensor is integrated into the microchip to detect molecules in the surrounding fluids. When the concentration of the molecules reaches a certain level, the sensor sends a signal to the microprocessor to open one or more reservoirs. The microprocessor directs power through the demultiplexer to the particular reservoir (s).

H. Current Control Methods

A method of reservoir opening and chemical release is based on rupturing the reservoir cap due to a change in the temperature of the materials in the reservoir or a change in the temperature of the material forming the reservoir cap. In a preferred embodiment, such temperature changes are induced using thin film resistors integrated onto the microchip itself or small, prefabricated chip resistors surface mounted onto the microchip or its associated packaging. The temperature change may be controlled by the amount of current that is passed through the resistor and the thermal properties of the material inside the reservoir or the reservoir cap material itself. Control over the amount of current applied and its duration of application can be controlled by a microprocessor, remote control, biosensor, or a combination of these devices.

Applications of the Microchip Devices

Passive and active microchip devices have numerous in vitro and in vivo applications. The microchip can be used in vitro to deliver small, controlled amounts of chemical reagents or other molecules to solutions or reaction mixtures at precisely controlled times and rates. Analytical chemistry and medical diagnostics are examples of fields where the microchip delivery device can be used. The microchip can be used in vivo as a drug delivery device. The microchips can be implanted into a patient, either by surgical techniques or by injection, or can be swallowed. The microchips provide delivery of drugs to animals or persons who are unable to remember or be ambulatory enough to take medication. The microchips further provide delivery of many different drugs at varying rates and at varying times of delivery.

EXAMPLES

The devices and methods described herein will be further understood by reference to the following non-limiting examples.

Examples 1-3 describe fabrication processes, and can be understood with reference to FIGS. 1-2. Example 1 describes a process for fabricating an active release microchip device having reservoir caps which rupture due to a temperature change caused by the application of an electric current to a thin film resistor located near the reservoir cap. Example 2 describes a process for fabricating an active release microchip device as in Example 1 except that the resistors are located in the reservoirs. Example 3 describes a process for fabricating a passive release microchip device. Examples 4-7 describe in detail various embodiments of the microchip devices.

Example 1

Fabrication of an Active Release Microchip Having Resistors Near the Reservoir Cap 1) Obtain double side polished, prime grade, (100) oriented silicon wafers, i.e., substrates.
   Wafer thickness=approximately 295-310 μm
2) Deposit approximately 1600-1900 Å of low stress (10:1, silicon rich) silicon nitride on both sides of the wafers in an SVG/Thermco 7000 Series vertical tube reactor (VTR), 300a/300b/300c/300d.
   Gas Flows: Ammonia ($NH_3$)=24 sccm
   Dichlorosilane ($SiH_2Cl_2$)=253 sccm
   Chamber Pressure=268 mtorr; Temperature=780° C.
   Deposition Rate=approximately 30 Å/min.
3) Pattern positive photoresist (PR) as squares (approximately 500 μm by 500 μm) serving as the large reservoir openings on one side of the wafers having low stress silicon nitride deposited on them.
   Hexamethyldisilazane deposition on both sides of the wafer
     ("HMDS vapor prime") in vacuum oven approximately 30 min. at 150° C.
   Photoresist (PR) Type—OCG825-20
   PR Spin Speed and Times (for a Solitec Inc. Model 5110 spinner)
     7 sec. at 500 rpm (coat); 7 sec. at 750 rpm (spread); and 30 sec. at 3500 rpm (spin)
   Prebake (in Blue M Model DDC-146C oven): 30 min. at 90° C.
   Ultra-violet (UV) exposure for each wafer in the contact alligner (Karl Suss Model MA4) with patterned mask
     32 sec. at wavelength=320 nm
   Developer Type—OCG934 1:1
   Put exposed wafers into slightly agitated, room temperature developer
     Develop Time=approximately 40 seconds
     Cascade Rinse=2 min.
     Rinse and Dry Wafers in Spin Rinse Dryer (SRD)
     Postbake (in Blue M Model DDC-146C oven): 30 min. at 120° C.

4) Etch the VTR nitride to the underlying silicon using a plasma etcher (Plasmaquest Series II Reactor Model 145), 320a/320b/320c/320d.

Gas Flows: Oxygen ($O_2$)=2 sccm; Helium (He)=15 sccm; and

Carbon Tetrafluoride ($CF_4$)=15 sccm

Power: RF=10 W; ECR=100 W

Chamber Pressure=20 mtorr; Temperature=25° C.

Nitride Etch Rate=approximately 350 Å/min

5) Remove excess PR with solvents—acetone, methanol, isopropanol.

6) Etch the exposed silicon in aqueous potassium hydroxide (KOH) in a wet processing hood (by Semifab, Inc.), 340a/340b/340c/340d.

Concentration=approximately 38-40% by weight

Temperature=approximately 85-90° C.

Etch Rate=approximately 1 μm/min

7) Post-KOH clean in a wet processing hood (by Laminaire Corp.) to avoid $K^+$ contamination in cleanroom.

Piranha Clean for 15 min.

Dump Rinse=3 times

Hydrofluoric Acid (HF) Dip: 10 sec. in 50:1 water:HF solution (by vol.)

Dump Rinse=3 times

Standard RCA clean

Rinse and Dry in SRD

8) Pattern image reversal PR near the nitride membranes for subsequent platinum liftoff process.

HMDS vapor prime in vacuum oven: approximately 30 min. at 150° C.

Photoresist Type (PR)—AZ 5214 E

PR Spin Speed and Times (for a Solitec Inc. Model 5110 spinner)

6 sec. at 500 rpm (coat); 6 sec. at 750 rpm (spread); and 30 sec. at 4000 rpm (spin)

Prebake (in Blue M Model DDC-146C oven): 30 min. at 90° C.

Ultra-violet (UV) exposure for each wafer in the contact aligner (Karl Suss Model MA4) with patterned mask 40 sec. at wavelength=320 nm Bake for 90 sec. on a metal plate in an oven at 120° C. (Blue M Model DDC-146C)

UV flood exposure for each wafer in the contact alligner (Karl Suss Model MA4) WITHOUT a patterned mask (expose entire wafer)

Approximately 200 sec. at wavelength=320 nm

Developer Type—AZ 422 MIF

Put exposed wafers into slightly agitated, room temperature developer

Develop Time=approximately 1 min. 30 sec.

Cascade Rinse=2 min.

Rinse and Dry Wafers in Spin Rinse Dryer (SRD)

9) Evaporation of platinum onto the image reversal PR patterned side of each wafer using a liftoff plate (wafer holder) in an electron beam evaporator (Temescal Semiconductor Products Model VES 2550).

Platinum Deposition Rate=5 Å/sec.

Platinum Thickness=approximately 3000 Å

Base Pressure=approximately $5.0 \times 10^{-7}$ torr

Room Temperature (no outside heating or cooling)

10) Liftoff platinum layer with acetone, 360a/360b.

11) Clean wafers with solvents—acetone, methanol, isopropanol.

12) Oxygen plasma clean (ash) in a plasma etcher (Plasmaquest Series II Reactor Model 145).

Gas Flows: $O_2$=25 sccm; He=15 sccm

Power: RF=10 W; ECR=200 W

Chamber Pressure=20 mtorr; Temperature=25° C.

13) Deposit plasma-enhanced chemical vapor deposition (PECVD) silicon dioxide over the entire surface of the wafers having the platinum resistors on them using a PECVD chamber (Plasma-Therm 700 Series Waf'r/Batch Dual Chamber Plasma Processing System).

Gas Flows: 2% $SiH_4$ in $N_2$=400 sccm; $N_2O$=900 sccm

RF Power=20 W

Chamber Pressure=900 mtorr; Temperature=350° C.

Deposition Rate=approximately 250-500 Å/min.

14) Clean wafers with solvents, such as acetone, methanol, isopropanol.

15) Pattern PR to expose portions of the silicon dioxide covering parts of the platinum resistors 390a/380b. (The inclusion of an oxide layer, as described in steps 13, 14, and 15 is optional.)

HMDS vapor prime in vacuum oven: approximately 30 min. at 150° C.

Photoresist (PR) Type—OCG825-20

PR Spin Speed and Times (for a Solitec Inc. Model 5110 spinner)

7 sec. at 500 rpm (coat); 7 sec. at 750 rpm (spread); and 30 sec. at 3500 rpm (spin)

Prebake (in Blue M Model DDC-146C oven): 30 min. at 90° C.

Ultra-violet (UV) exposure for each wafer in the contact alligner (Karl Suss Model MA4) with patterned mask 32 sec. at wavelength=320 nm Developer Type—OCG934 1:1

Put exposed wafers into slightly agitated, room temperature developer

Develop Time=approximately 55 sec.

Cascade Rinse=2 min.

Rinse and Dry Wafers in Spin Rinse Dryer (SRD)

Postbake (in Blue M Model DDC-146C oven): 30 min. at 120° C.

16) Etch the exposed silicon dioxide to the platinum surface with a plasma etcher (Plasmaquest Series II Reactor Model 145).

Gas Flows: He=15 sccm; $CF_4$=15 sccm

Power: RF=10 W; ECR=100 W

Chamber Pressure=20 mtorr; Temperature=15° C.

Silicon Dioxide Etch Rate=approximately 215 Å/min.

17) Etch (e.g., completely remove) the nitride membrane from the back of the devices with a plasma etcher (Plasmaquest Series II Reactor Model 145).

Gas Flows: $O_2$=2 sccm; He=15 sccm; and $CF_4$=15 sccm

Power: RF=10 W; ECR=100 W

Chamber Pressure=20 mtorr; Temperature=25° C.

Nitride Etch Rate=approximately 350 Å/min.

18) Use a microinjector (World Precision Instruments Ultra Micro Pump-UMP II) to inject a solution of a thermally responsive polymer into the large reservoir openings 400b. Capillary action and surface tension keep the material from running out of the small opening of the reservoir.

19) Allow the solvent in the thermally responsive polymer solution to evaporate, resulting in the formation of a solid polymeric reservoir cap covering the small reservoir opening 420b.

The drying time and temperature depend on the particular solvent used in the polymer solution (e.g., water takes longer to evaporate than methanol).

20) Use a microinjector or other filling technique to fill the reservoir with release system 400a/420a (and implied step between 420b and 440b) and then seal the large reservoir opening by bonding a backing plate across the large opening side of the substrate 440*a*/440*b*.
21) Dice the wafers with a diesaw (Disco Automatic Dicing Saw Model DAD-2H/6T).
   Process yields 21 devices per 4" wafer with each device measuring 17 mm by 17 mm on a side
Fabrication of the active microchip devices having resistors near the reservoir caps is complete.

This method can readily be modified by changing the order of some of the process steps to utilize other methods of forming the temperature responsive reservoir caps. For example, the cap material can be spin coated onto the surface of the silicon wafer having reservoir openings covered by nitride membranes, the cap material can be patterned by photolithography, and etched by chemical or dry etching methods to form reservoir caps 380*a*. Using these techniques, reservoir caps of any shape, size, and placement can be formed (compare for example reservoir caps in 440*a* with 440*b*).

Alternatively, the order of the process steps and the pattern on the photolithography masks described above in this example can be easily modified to allow the resistors to be fabricated directly on top of or directly below the reservoir cap material.

Example 2

Fabrication of an Active Release Microchip Having Resistors in the Reservoirs 1) thru 7) The steps for producing a first wafer containing nitride membrane covered reservoirs are the same as in Example 1.
8) Pattern image reversal PR on a second wafer 370*a*/370*b* (e.g., silicon wafer or other substrate such as glass) for subsequent platinum liftoff process.
   HMDS vapor prime in vacuum oven: approximately 30 min. at 150° C.
   Photoresist Type (PR)—AZ 5214 E
   PR Spin Speed and Times (for a Solitec Inc. Model 5110 spinner)
      6 sec. at 500 rpm (coat); 6 sec. at 750 rpm (spread); and 30 sec. at 4000 rpm (spin)
   Prebake (in Blue M Model DDC-146C oven): 30 min. at 90° C.
   Ultra-violet (UV) exposure for each wafer in the contact aligner
      (Karl Suss Model MA4) with patterned mask
      40 sec. at wavelength=320 nm
   Bake for 90 sec. on a metal plate in an oven at 120° C. (Blue M Model DDC-146C)
   UV flood exposure for each wafer in the contact aligner (Karl Suss Model MA4) WITHOUT a patterned mask (expose entire wafer)
      Approximately 200 sec. at wavelength=320 nm
      Developer Type—AZ 422 MIF
   Put exposed wafers into slightly agitated, room temperature developer
      Develop Time=approximately 1 min. 30 sec.
      Cascade Rinse=2 min.
      Rinse and Dry Wafers in Spin Rinse Dryer (SRD)
9) Evaporation of platinum onto the image reversal PR patterned side of the second wafer using a liftoff plate (wafer holder) in an electron beam evaporator (Temescal Semiconductor Products Model VES 2550).
   Platinum Deposition Rate=5 Å/sec.
   Platinum Thickness=approximately 3000 Å
   Base Pressure=approximately $5.0 \times 10^{-7}$ torr
   Room Temperature (no outside heating or cooling)
10) Liftoff platinum layer with acetone, 372*a*/372*b*.
11) Clean the second wafer with solvents—acetone, methanol, isopropanol.
12) Oxygen plasma clean (ash) the second wafer in a plasma etcher (Plasmaquest Series II Reactor Model 145).
   Gas Flows: $O_2$=25 sccm; He=15 sccm
   Power: RF=10 W; ECR=200 W
   Chamber Pressure=20 mtorr; Temperature=25° C.
13) Use a microinjector (World Precision Instruments Ultra Micro Pump—UMP II) to inject release system and molecules, or any combination thereof, into the reservoirs of the first wafer 360*c*/360*d* (identical to 380*c*/380*d*).
14) Align the resistors on the second wafer with the reservoirs of the first wafer 400*c*/400*d* and bond the two wafers together using chemical or thermal adhesives or using standard Si—Si or Si-glass bonding techniques (e.g., anodic bonding) 420*c*/420*d*.
15) Dice the wafers with a diesaw (Disco Automatic Dicing Saw Model DAD-2H/6T).
   Process yields 21 devices per 4" wafer with each device measuring 17 mm by 17 mm on a side
Fabrication of the active microchip devices having resistors in the reservoirs is complete.

The etch mask material in the final product shown in FIG. 2*c* either serves as a rupturable reservoir cap 420*c*, or alternatively is replaced on the release side (distal the resistors) with a layer of a reservoir cap material that is either rupturable or is a permeable or semi-permeable membrane material. In the latter case, the permeability is temperature dependent, such that molecules in the reservoir pass through the membrane (i.e., reservoir cap) at a negligible rate or not at all when the resistors are not activated or when the temperature is below a selected threshold temperature. However, upon heating of the membrane, by activation of the resistors and/or by elevation in the environmental temperature (above the selected threshold temperature) in which the microchip is situated, the membrane (i.e., reservoir cap) becomes sufficiently permeable to allow release of molecules from the reservoir. In this embodiment, activation and deactivation of the resistors, whether positioned in the reservoir or near the reservoir cap can function as an on/off switch to control release of molecules from the reservoir.

Alternatively, as shown in FIG. 2*d*, the etch mask material in the final product shown is removed on the release side (distal the resistors) 440*d*. In this embodiment, no reservoir cap is provided, such that the release of molecules from the reservoir is thermally controlled by the selection of a solid or gel release system which releases negligible or no molecules from the reservoir when the resistors are not activated or when the temperature is below a selected threshold temperature. However, upon heating, by activation of the resistors and/or by elevation in the environmental temperature, the release system releases the molecules, for example, by having the release system or a portion thereof undergo a phase change (e.g., melt, vaporize, sublime, dissolve), by having a degradable matrix portion of the release system degrade or undergo a reaction, or by having a release system matrix change its permeability.

Example 3

Fabrication of a Passive Release Microchip

1) Obtain double side polished, prime grade, (100) oriented silicon wafers for devices having reservoirs extending completely through the wafer or single side polished, prime grade, (100) oriented silicon wafers for devices having reservoirs that do not extend completely through the wafer.

Wafer thickness=approximately 295-310 μm for devices with reservoirs extending completely through the wafer (devices that do not have reservoirs extending all the way through the wafer can be of any desired thickness)

2) Deposit approximately 1600-1900 Å of low stress (10:1, silicon rich) silicon nitride on both sides of the wafers in an SVG/Thermco 7000 Series vertical tube reactor (VTR) 30.

Gas Flows: Ammonia ($NH_3$)=24 sccm
Dichlorosilane ($SiH_2Cl_2$)=253 sccm
Chamber Pressure=268 mtorr; Temperature=780° C.
Deposition Rate=approximately 30 Å/min.

3) Pattern positive PR as squares (approximately 500 μm by 500 μm for devices with reservoirs extending completely through the wafer or any desired dimension for devices that do not have reservoirs extending all the way through the wafer) serving as the large reservoir openings on one side of the wafers having low stress silicon nitride deposited on them 32.

Hexamethyldisilazane deposition on both sides of the wafer ("HMDS vapor prime") in vacuum oven approximately 30 min. at 150° C.
Photoresist (PR) Type—OCG825-20
PR Spin Speed and Times (for a Solitec Inc. Model 5110 spinner)
  7 sec. at 500 rpm (coat); 7 sec. at 750 rpm (spread); and
  30 sec. at 3500 rpm (spin)
Prebake (in Blue M Model DDC-146C oven): 30 min. at 90° C.
Ultra-violet (UV) exposure for each wafer in the contact alligner (Karl Suss Model MA4) with patterned mask
  32 sec. at wavelength=320 nm
Developer Type—OCG934 1:1
Put exposed wafers into slightly agitated, room temperature developer
Develop Time=approximately 40 seconds
Cascade Rinse=2 min.
Rinse and Dry Wafers in Spin Rinse Dryer (SRD)
Postbake (in Blue M Model DDC-146C oven): 30 min. at 120° C.

4) Etch the VTR nitride to the underlying silicon using a plasma etcher (Plasmaquest Series II Reactor Model 145) 32.

Gas Flows: Oxygen ($O_2$)=2 sccm; Helium (He)=15 sccm
Carbon Tetrafluoride ($CF_4$)=15 sccm
Power: RF=10 W; ECR=100 W
Chamber Pressure=20 mtorr; Temperature=25° C.
Nitride Etch Rate=approximately 350 Å/min.

5) Remove excess PR with solvents—acetone, methanol, isopropanol.

6) Etch the exposed silicon in aqueous potassium hydroxide (KOH) in a wet processing hood (by Semifab, Inc.) 34.

Concentration=approximately 38-40% by weight
Temperature=approximately 85-90° C.
Etch Rate=approximately 1 μm/min.

7) Post-KOH clean in a wet processing hood (by Laminaire Corp.) to avoid $K^+$ contamination in cleanroom.

Piranha Clean for 15 min.
Dump Rinse=3 times
Hydrofluoric Acid (HF) Dip
10 sec. in 50:1 water:HF solution (by volume)
Dump Rinse=3 times
Standard RCA clean
Rinse and Dry in SRD For those devices not having a nitride membrane (reservoirs not extending completely through the wafer), fabrication of passive microchip device is complete. Dice the wafers into individual devices. The reservoirs of each device are ready to be filled.

Alternately, for those devices having a nitride membrane (reservoirs extend completely through the wafer), continue with the following steps:

8) Fill the reservoir using injection, inkjet printing, spin coating or another method with reservoir cap material 36a/36b/38a/38b, release system 40a/40b/42, or any combination thereof. The composition of the reservoir cap materials and/or release system can be varied for each reservoir in order to change the disintegration rate of the reservoir cap or release system or the diffusion rate of the drug through the reservoir cap or release system at a particular environmental temperature (e.g., human body temperature, 37° C.).

9) Seal the reservoir openings on the side of the wafer through which the reservoirs were filled 44.

10) Etch the nitride membranes on the side of the wafer opposite the filling side by using a plasma etcher (Plasmaquest Series II Reactor Model 145) until the cap material or release system is reached (etch parameters may vary depending on the type of cap material or release system under the nitride) 46.

Gas Flows: Oxygen ($O_2$)=2 sccm; Helium (He)=15 sccm
Carbon Tetrafluoride ($CF_4$)=15 sccm
Power: RF=10 W; ECR=100 W
Chamber Pressure=20 mtorr; Temperature=25° C.
Nitride Etch Rate=approximately 350 Å/min.

11) Spin photoresist on the side of the wafers having exposed cap materials or release system to protect them during wafer dicing (this step may not be necessary, depending on the type of exposed cap material or release system).

Photoresist (PR) Type—OCG825-20
PR Spin Speed and Times (for a Solitec Inc. Model 5110 spinner)
  7 sec. at 500 rpm (coat); 7 sec. at 750 rpm (spread); and
  30 sec. at 3500 rpm (spin)
Prebake (in Blue M Model DDC-146C oven): 30 min. at 90° C.

12) Dice the wafers with a diesaw (Disco Automatic Dicing Saw Model DAD-2H/6T).

Process yields 21 devices per 4" wafer with each device measuring 17 mm by 17 mm on a side 13) Clean the devices with solvents and $O_2$ plasma (these steps may not be necessary, depending on the type of exposed cap material or release system).

Solvent clean—acetone, methanol, isopropanol
Oxygen plasma clean in a plasma etcher (Plasmaquest Series II Reactor Model 145)
Gas Flows: $O_2$=25 sccm; He=15 sccm
Power: RF=10 W; ECR=200 W
Chamber Pressure=20 mtorr; Temperature=25° C.

Fabrication of the passive microchip devices is complete.

Example 4

Microchip with Passive Timed Molecule Release

A passive timed release device, microchip 10 is shown in FIG. 4. Microchip 10 is formed from substrate 14. Reservoirs 16 are etched into substrate 14. Positioned in reservoirs 16 is a release system containing molecules 18 for delivery. The reservoirs are capped with reservoir caps 12. The release system and the molecules for delivery 18 can vary between rows 20a, 20b, 20c, and within reservoirs of each row of the array.

FIGS. 7a-i depict several additional possible configurations for passive delivery devices. How the release of molecules from such passive device configurations is influenced by temperature can best be understood in view of the following examples and considerations. There are polymers that do not degrade at room temperature, but can degrade at slightly higher temperatures, depending on the polymer's composition. Therefore, a passive microchip device can be fabricated with each reservoir having reservoir caps or release systems of slightly different polymer compositions. At room temperature, all the reservoir caps and release systems remain stable and do not release molecules. However, if the entire device is raised to slightly higher temperatures, selected reservoir caps and release systems will start to degrade. Therefore, the exposure of the device to a particular temperature can enable molecule release from a passive microchip to be controlled. The permeability of a non-degradable polymer can also be temperature and composition dependent in much the same way, making the selection of degradable or non-degradable materials, or any combination thereof, dependent on the molecule to be released, the device's particular application, and the desired time and rate of molecule release.

Example 5

Microchip with Active Controlled Time Release

A drug delivery device that provides active timed release is shown as microchip 100 in FIG. 5. Microchip 100 includes substrate 130, in which reservoirs 160 are filled with release system containing molecules 180 for delivery. Microchip 100 also includes reservoir caps 120a/120b, and resistors 140a/140b. FIG. 5 illustrates just two of the many possible configurations of resistors. Here, three of the reservoirs are provided with resistors 140a positioned near reservoir caps 120a, while the other three reservoirs are provided with resistors 140b positioned on top of reservoir caps 120b. Preferably, microchip 100 further includes an input source, a microprocessor, a timer, a demultiplexer, and a power source (not shown). The power source provides electric current to the resistors to cause the temperature of the reservoir caps near the resistors to rise. Upon application of a small current to a resistor, the local temperature rise of the nearest reservoir caps causes those reservoir caps to rupture by heat induced expansion or contraction or by a phase change in the reservoir cap material (e.g., melting) that causes the reservoir cap to lose its structural integrity. Once the reservoir cap is ruptured or melted, the release system containing the molecules for delivery 180 is exposed to the surrounding environment and release from that reservoir begins. The microprocessor directs power to specific electrode pairs through a demultiplexer as directed by a PROM, remote control, or biosensor.

FIGS. 8a-d depicts four additional possible configurations for the resistors and reservoir caps in the active delivery devices. The resistors in FIG. 8a are placed near the reservoir cap, outside the reservoir. The resistor in FIG. 8b are placed on top of the reservoir cap. The resistors are placed within the reservoirs in FIGS. 8c-d. As in Example 5, the selection of degradable or non-degradable materials, or any combination thereof, is dependent on the molecule to be released, the device's particular application, and the desired time and rate of molecule release. Placement of the resistors with respect to degradable or non-degradable reservoir caps or release systems is dependent on where the heat needs to be applied to get optimal molecule release. For example, if a reservoir cap needs direct heat to either cause it to rupture or become more permeable, the best location for the resistor may be directly on top of or directly below the reservoir cap material, instead of near the cap or at the bottom of the reservoir. The placement of the reservoir cap on top of or slightly inside the reservoir will depend on the cap fabrication methods compatible with the cap material.

Example 6

Microchip Devices Having Complex Substrates

FIGS. 6a-d illustrate several typical variations of the devices, active or passive release, wherein two or more substrate portions are attached to one another to form, for example, a larger or composite substrate. FIG. 6a, for comparison, shows a "single" substrate device 500, which has substrate 510, in which reservoirs 520 are filled with molecules to be released 540. Reservoirs 520 are covered by reservoir caps 530 and sealed with backing plate 550 or other type of seal. Resistors 560 are placed near reservoir caps 530.

FIG. 6b shows device 600 having a substrate formed of a top substrate portion 610a bonded to bottom substrate portion 610b. Reservoirs 620a, in top substrate portion 610a are in communication with reservoirs 620b in bottom substrate portion 610b. Reservoirs 620a/620b are filled with molecules to be released 640 and are covered by reservoir caps 630 and sealed with backing plate 650. Resistors 660 are placed near reservoir caps 630.

FIG. 6c shows device 700 having a substrate formed of a top substrate portion 710a bonded to bottom substrate portion 710b. Top substrate portion 710a has reservoir 720a which is in communication with reservoir 720b in bottom substrate portion 710b. Reservoir 720b is much larger than reservoir 720a and reservoirs 720a/720b contain molecules to be released 740. Reservoirs 720a/720b are filled with molecules to be released 740 and are covered by reservoir cap 730 and sealed with backing plate 750. Resistors 760 are placed near reservoir caps 730.

FIG. 6d shows device 800 having a substrate formed of a top substrate portion 810a bonded to bottom substrate portion 810b. Top substrate portion 810a has reservoir 820a which contains first molecules to be released 840a. Bottom substrate portion 810b has reservoir 820b which contains second molecules to be released 840b. First molecules to be released 840a can be the same or different from second molecules to be released 840b. Reservoir 820a is covered by reservoir cap 830a and sealed by reservoir cap 830b and partially by bottom substrate portion 810b. Reservoir 820b is covered by reservoir cap 830b and sealed with backing plate 850. Resistors 860a are placed near reservoir caps 830a, and resistors 860b are placed near reservoir caps 830b.

FIG. 6e shows another reservoir shape configuration.

Example 7

Microchip Devices with Release Caused By Cooling

Active and passive microchips can release molecules by the cooling of the device, release systems, or reservoir caps. In one active microchip embodiment, the reservoir cap material is under less mechanical stress when kept at a temperature higher than room temperature. The temperature of the reservoir caps is kept higher than room temperature by applying current to resistors placed on or near the reservoir caps. When release is desired from a particular reservoir, the current supplied to that reservoir cap's resistors can be turned off, essentially removing the reservoir cap's source of heat. The temperature of the reservoir cap then decreases back to room temperature, causing the mechanical stresses in the reservoir cap to increase. The rate and magnitude of the increase in the mechanical stresses will depend on the cap's composition, placement, and thickness. Once the mechanical stress in the reservoir cap reaches a threshold level, the reservoir cap ruptures and releases the molecules stored in the reservoir.

Passive microchips can also release molecules in response to cooling. In one embodiment, the temperature of the environment surrounding the device is decreased, allowing mechanical stresses in the reservoir caps to increase. The rate and magnitude of the increase in the mechanical stresses will depend on the cap's composition, placement, and thickness. When the stresses in a reservoir cap exceed a certain threshold, the cap will rupture and release the molecules stored in the reservoir.

In another embodiment, a decrease in the temperature of the release system in a reservoir causes it to contract and exert an inward force on the reservoir cap in both active and passive devices, which will eventually cause it to rupture and release the molecules stored in the reservoir.

Modifications and variations of the methods and devices described herein will be obvious to those skilled in the art from the foregoing detailed description. Such modifications and variations are intended to come within the scope of the appended claims.

We claim:

1. A microchip device comprising:
   a substrate;
   a plurality of reservoirs in the substrate, each reservoir defining an internal volume; and
   a reservoir cap bounding the internal volume of each of said reservoirs from an external environment, the reservoir cap being formed of a material that undergoes a phase change upon heating,
   wherein the internal volume can communicate with the external environment upon heating said reservoir cap to cause said reservoir cap to undergo a phase change and rupture.

2. The device of claim 1, further comprising a means for heating said reservoir cap.

3. The device of claim 1, wherein said reservoir cap comprises a metal film.

4. The device of claim 1, wherein said reservoir cap can be heated and ruptured with substantially no heating of a material disposed in the internal volume.

5. The device of claim 1, wherein the internal volume comprises a protein.

* * * * *